United States Patent
Foss et al.

(10) Patent No.: US 6,723,428 B1
(45) Date of Patent: Apr. 20, 2004

(54) ANTI-MICROBIAL FIBER AND FIBROUS PRODUCTS

(75) Inventors: Stephen W. Foss, Rye Beach, NH (US); Dieter Keser, Exeter, NH (US); Alan Tefft, Newington, NH (US); Robert V. Sawvell, Jr., Columbia, SC (US); Steven R. Brown, East Hampstead, NH (US); Gordon Goodwin, Jr., Bradford, MA (US); Arthur H. Cashin, Hampton, NH (US); James M. Parlier, Manchester, NH (US); Kim Goudreault, Bradford, MA (US)

(73) Assignee: Foss Manufacturing Co., Inc., Hampton, NH (US)

( * ) Notice: Subject to any disclaimer, the term of this patent is extended or adjusted under 35 U.S.C. 154(b) by 0 days.

(21) Appl. No.: 09/565,138

(22) Filed: May 5, 2000

Related U.S. Application Data

(60) Provisional application No. 60/181,251, filed on Feb. 9, 2000, provisional application No. 60/180,536, filed on Feb. 7, 2000, provisional application No. 60/180,240, filed on Feb. 4, 2000, provisional application No. 60/173,207, filed on Dec. 27, 1999, provisional application No. 60/172,285, filed on Dec. 17, 1999, provisional application No. 60/172,533, filed on Dec. 17, 1999, and provisional application No. 60/136,261, filed on May 27, 1999.

(51) Int. Cl.[7] .................................................. D01F 8/00
(52) U.S. Cl. ........................ 428/370; 428/375; 428/324
(58) Field of Search ............................... 428/374, 370, 428/373, 372

(56) References Cited

U.S. PATENT DOCUMENTS

| 3,959,556 A | 5/1976 | Morrison |
|---|---|---|
| 3,983,061 A | 9/1976 | Oxe et al. |
| 4,226,232 A | 10/1980 | Spence |
| 4,350,732 A | 9/1982 | Goodwin |
| 4,371,577 A | 2/1983 | Sato et al. |
| 4,401,770 A | 8/1983 | Hance |
| 4,624,679 A | 11/1986 | McEntee |
| 4,864,740 A | 9/1989 | Oakley |
| 4,911,898 A | 3/1990 | Hagiwara et al. |
| 4,919,998 A | 4/1990 | Goad et al. |
| 4,923,914 A | 5/1990 | Nohr et al. |
| 4,938,958 A | 7/1990 | Niira et al. |
| 5,047,448 A | 9/1991 | Tanaka et al. |
| 5,071,551 A | 12/1991 | Muramatsu et al. |
| 5,094,847 A | 3/1992 | Yazaki et al. |

(List continued on next page.)

FOREIGN PATENT DOCUMENTS

| JP | 1246204 A2 | 10/1989 |
|---|---|---|
| JP | 2091009 A2 | 3/1990 |
| JP | 2099606 A2 | 4/1990 |
| JP | 2169740 A2 | 6/1990 |
| JP | 611872 A2 | 4/1994 |

*Primary Examiner*—N. Edwards
(74) *Attorney, Agent, or Firm*—Perkins, Smith & Cohen; Jerry Cohen; Harvey Kaye

(57) ABSTRACT

An anti-microbial and/or anti-fungal synthetic fiber and various products made partially or wholly therefrom. The fiber comprises various thermoplastic polymers and additives in a mono-component form or a bi-component form in either a core-sheath or side-by-side configurations. The anti-microbial synthetic fibers comprise inorganic anti-microbial additives, distributed in certain areas to reduce the amount of the anti-microbial agents being used, and therefore the cost of such fibers. The fibers can incorporate anti-microbial additives so that they are not removed by repeated washing in boiling water and in dry clean cycles and become ineffective and conversely enhance access to the additives by washing or the like. The fibers comprise high tenacity polymers (e.g. PET) in one portion and hydrolysis resistance polymers (e.g. PCT) in another portion with the additives. The fibers can further be blended with non-anti-microbial fibers such as cotton, wool, polyester, acrylic, nylon etc. to provide anti-microbial finished fabrics.

17 Claims, 15 Drawing Sheets

U.S. PATENT DOCUMENTS

| | | |
|---|---|---|
| 5,098,417 A | 3/1992 | Yamazaki et al. |
| 5,104,934 A | 4/1992 | Udipi |
| 5,106,897 A | 4/1992 | Chen |
| 5,134,201 A | 7/1992 | Billovits et al. |
| 5,147,339 A | 9/1992 | Sundstrom |
| 5,180,585 A | 1/1993 | Jacobson et al. |
| 5,187,230 A | 2/1993 | Udipi |
| 5,219,325 A | 6/1993 | Hennink et al. |
| 5,244,667 A | 9/1993 | Hagiwara et al. |
| 5,268,203 A | 12/1993 | Batdorf |
| 5,300,167 A | 4/1994 | Nohr et al. |
| 5,405,644 A | 4/1995 | Ohsumi et al. |
| 5,408,022 A | 4/1995 | Imazato et al. |
| 5,494,987 A | 2/1996 | Imazato et al. |
| 5,525,651 A | 6/1996 | Ogoe et al. |
| 5,709,870 A | 1/1998 | Yoshimura et al. |
| 5,733,949 A | 3/1998 | Imazato et al. |
| 5,756,578 A | 5/1998 | Hanes |
| 5,762,650 A | 6/1998 | Ruggiero et al. |
| 5,783,570 A | 7/1998 | Yokota et al. |
| 5,876,489 A | 3/1999 | Kunisaki et al. |
| 5,900,258 A | 5/1999 | Engler |
| 5,958,539 A | 9/1999 | Eckart et al. |
| 5,985,079 A | 11/1999 | Ellison |
| 6,037,057 A | 3/2000 | Hartzog et al. |

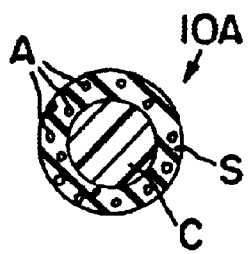
FIG. IA
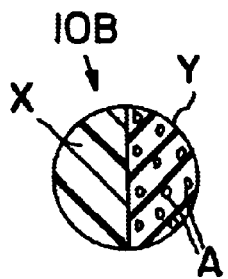
FIG. IB
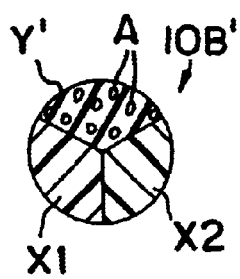
FIG. IB'
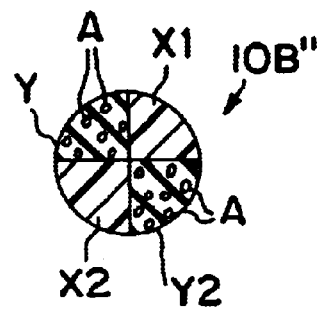
FIG. IB"
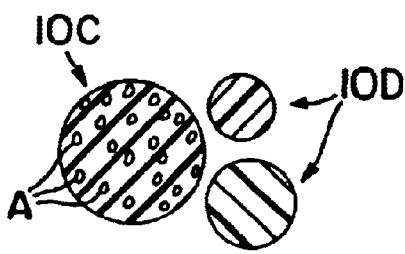
FIG. IC
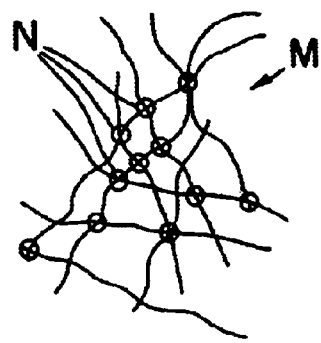
FIG. 2

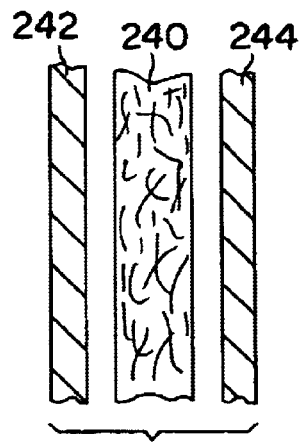
F I G. 27
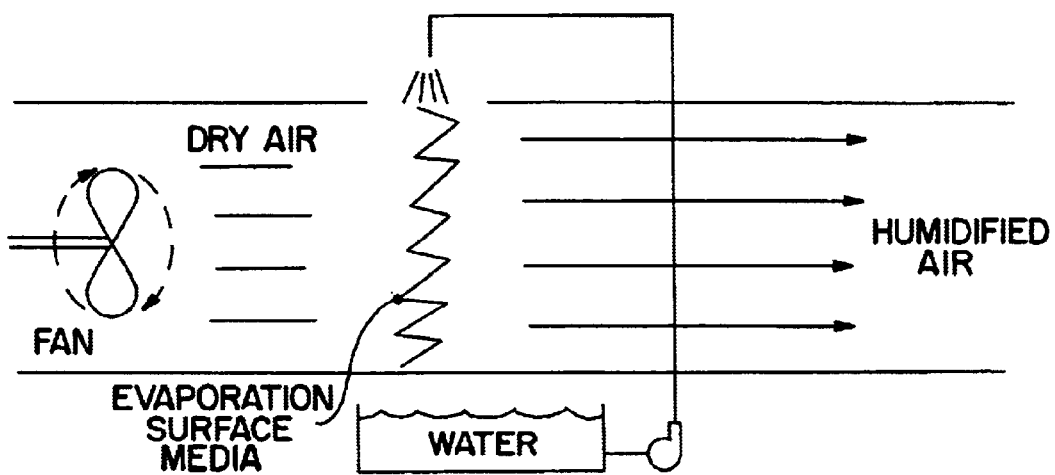
F I G. 28

ANTI-MICROBIAL FIBER AND FIBROUS PRODUCTS

CROSS-REFERENCE TO RELATED APPLICATIONS

The present application claims the priority of the following provisional applications: Ser. No. 60/136,261, filed May 27, 1999; Ser. No. 60/173,207, filed Dec. 27, 1999; Ser. No. 60/172,285, filed Dec. 17, 1999; Ser. No. 60/172,533, filed Dec. 17, 1999; Ser. No. 60/180,536, filed Feb. 7, 2000; Ser. No. 60/18,1,251, filed Feb. 9, 2000; and Ser. No. 60/180,240, filed Feb. 4, 2000.

FIELD OF THE INVENTION

The present invention relates generally to fiber, and, more particularly to a fiber having anti-microbial (and/or anti-fungal) properties which remain with the fiber when used in a fabric product after repeated launderings/uses. More specifically it provides a wholly or partly synthetic fiber and multi- or mono-component anti-microbial and/or anti-fungal synthetic fibers, alone or integrated with other synthetic or natural fibers, using various thermoplastic polymers and additives. It may be a bi-component fiber having either a core-sheath or side-by-side configuration or other configurations (e.g. pie-wedge). One arrangement uses binder fibers, which are staple fiber or filament.

The present invention further relates to products made wholly or in part of such fiber.

There is an incontinent garment [invention] embodiment which relates generally to garments and other articles, and, more particularly, to garments and other articles which have anti-microbial properties for people who are incontinent. Such garments and articles include underwear, pajamas, washable and/or disposable diapers, as well as linens, and bed packs for bed ridden patients, to prevent bed sores. Such garments and articles may be made of woven fabric, knitted fabric or non-woven fabric.

There is an air filter embodiment which relates to vehicle and aircraft cabin air filters that are made of a wholly or partly synthetic fiber that can be either mono- or multi-component in nature and has anti-microbial properties and can be used with other synthetic or natural fibers to form a variety of fabrics and materials. Such invention provides for filter materials that are resistant to bacterial and fungal growth as well as to the deterioration of the fibers contained in these filter materials.

There is a dressings embodiment which relates to wound care materials and burn dressings formed of fibers and/or fabrics made of a wholly or partly synthetic fiber that can be either mono- or multi-component in nature and has anti-microbial properties and can be used with other synthetic or natural fibers to form a variety of different types of fabrics and materials suitable for these uses. The invention provides wound care dressings and burn dressings for suppressing bacterial and fungal growth, and the related risk of infection, in materials used for wound care dressings and burn dressings.

There is a fabric embodiment which relates generally to fabric construction, and, more particularly, to fabric having qualities imparted to it which remain for the life of the fabric, such as excellent color fastness without the need for a dye bath.

There is a footwear components embodiment which relates generally to the footwear art, and, more particularly, to footwear components having anti-microbial properties.

There is a wide sheet embodiment which relates to wide sheet materials that are made of a wholly or partly synthetic material and having anti-microbial and anti-fungal properties. Such sheets can be used with other synthetic or natural materials to form a variety of different end use products. This invention provides for sheet materials for end use products that are resistant to bacterial and fungal growth as well as to the deterioration of the agents contained in these materials.

There is also a shoe embodiment which relates to insoles and other shoe products.

There is a laminate embodiment which relates to generally to laminate materials, and, more particularly that are made of a wholly thermoplastic stiff reinforcing multiple laminate moldable into compound shapes and bondable via a thermoplastic hot melt adhesive to a carrier surface to be reinforced and suitable for footwear.

There is an institutional and home furnishings embodiment which relates to bed sheets, pillow cases, mattress pads, blankets, towels, drapes, bedspreads, pillow shams, carpets, walk-off mats, napkins, linens, wall coverings, upholstered furniture, liners, mattress ticking, mattress filling, pillow filling, carpet pads, upholstery fabric and the like. It includes fabrics and materials, and also support substrates and products constructed using generally a wholly or partly synthetic fiber (which may be mixed with natural fibers) that can be either mono- or multi-component in nature and has anti-microbial properties. These are for use in the home, or in institutional settings such as hotels and motels, adult communities, offices, hospitals, nursing homes, and prisons.

There is a medical-healthcare embodiment which relates to medical/healthcare wipes possessing anti-microbial properties, more particularly, to such wipes made of materials and fabrics composed of a wholly or partly synthetic fiber that can be either mono- or multi-component in nature and having anti-microbial properties and can be used with other synthetic or natural fibers. The invention provides wipes for suppressing bacterial and fungal growth, and the related risk of infection. Such wipes are usually disposable.

BACKGROUND OF THE INVENTION

There is a growing interest today in products which have anti-microbial and anti-fungal properties. There are a number of additives, fibers and products on the market which claim to have these properties. However, many do not have such properties, or the properties do not remain for the life of the product, or they have adverse environmental consequences.

Various materials have been used in the past to provide anti-microbial and anti-fungal properties to fibers and fabrics.

Examples of some organic types of anti-microbial agents, are U.S. Pat. No.: 5,408,022 and U.S. Pat. No. 5,494,987 (an anti-microbial polymerizable composition containing an ethylenically unsaturated monomer, a specific one-, di- or tri-functional anti-microbial monomer and a polymerization initiator which can yield an unreleasable anti-microbial polymer from which the anti-microbial component is not released), U.S. Pat. No. 5,709,870 (a silver containing anti-microbial agent which comprises carboxymethylcellulose, a crosslinked compound, containing silver in the amount of 0.01 to 1% by weight and having a degree of substitution of carboxymethyl group of not less than 0.4 and the anti-microbial agent being a silver salt of carboxymethylcellulose, which is insoluble to water), U.S.

Pat. No. 5,783,570 (an organic solvent-soluble mucopolysaccharide consisting of an ionic complex of at least one mucopolysaccharide and a quaternary phosphonium, an antibacterial antithrombogenic composition comprising organic solvent-soluble mucopolysaccharide and an organic polymer material, an antibacterial antithrombogenic composition comprising organic solvent-soluble mucopolysaccharide and an inorganic antibacterial agent, and to a medical material comprising organic solvent-soluble mucopolysaccharide).

Examples of some inorganic types of anti-microbial agents are:

Japanese Patent No. 1246204 (1988) which discloses an anti-microbial thermoplastic article with copper a compound added to the melted polymer just before extruding, in which the anti-microbial material is said to be resistant to washing.

U.S. Pat. No. 5,180,585 which discloses an antimicrobial with a first coating providing the antimicrobial properties and a second coating as a protective layer. A metal having antimicrobial properties is used including silver which is coated with a secondary protective layer.

Japanese Patent No. 2099606 (1990) which discloses a fiber with anti-microbial properties made of a liquid polyester and inorganic micro particles of zinc silicate, both being added to the melted polymer after polymerization and just before extrusion.

The use of anti-microbial agents in connection with thermoplastic material is known from U.S. Pat. No. 4,624,679 (1986). This patent is concerned with the degradation of anti-microbial agents during processing. This patent states that thermoplastic compounds which are candidates for treatment with anti-microbial agents include material such as polyamides (nylon 6 or 6,6), polyvinyl, polyolefins, polyurethanes, polyethylene terephthalate, styrene-butadiene rubbers.

Japanese Patent No. 2091009 (1990) and U.S. Pat. No. 5,047,448 disclose an anti-microbial thermoplastic polymer with copper or zinc compounds and fine particles of Al, Ag, Fe and Zn compounds and a liquid polyester, in which the anti-microbial material is said to be resistant to washing.

Japanese Patent No. 2169740 (1990) discloses a thermoplastic fiber such as PET which uses silver, copper or zinc as an anti-microbial agent. There is a cellulose component which reduces the amount of thermoplastic with anti-microbial agent and reduces the cost.

Examples of inorganic types of anti-microbial agent which have zeolite with silver is disclosed in U.S. Pat. Nos. 4,911,898, 5,094,847, 4,938,958 (use of zeolite with exchangeable ions such as silver and others), U.S. Pat. No. 5,244,667 (an anti-microbial composition which involves use of partial or complete substitution of ion-exchangeable metal ion such a silver, copper, zinc and others), U.S. Pat. No. 5,405,644 (an anti-microbial fiber having a silver containing inorganic microbiocide and the silver ion is stated to have been supported by zeolite, among other materials, the purpose being to prevent discoloration).

Various products have been made using anti-microbial fibers. U.S. Pat. No. 5,071,551 discloses a water purifier having a secondary filter downstream of its primary filter for removing microorganisms and antimicrobial means disposed between the two filters use of an anti-microbial agent for a water purifier.

Japanese Patent No. 6116872 (1994) discloses a suede-like synthetic leather with an anti-microbial agent. It discloses the use of anti-microbial zeolite having an anti-microbial metal ion. It uses two fiber types and includes PET.

U.S. Pat. No. 5,733,949 discloses an anti-microbial adhesive composition for dental use. The composition was made by blending of a polymerizable monomer having alcoholic hydroxy group and water to a dental composition containing an anti-microbial polymerizable monomer and a polymerizable monomer having acidic group, and with a polymerization catalyst. Such composition has capability to improve adhesive strength between the tooth and the restorative material to prevent microbial invasion at the interface and kill microorganisms remaining in the microstructure.

U.S. Pat. No. 5,876,489 discloses a germ-removing filter with a filter substrate and an anti-microbial material dispersedly mixed into the filter substrate. The anti-microbial material is an ion exchange fiber bonded with silver ion. In the ion exchange fiber, silver ions capable of killing living germs through an ion exchange reaction.

U.S. Pat. No. 5,900,258 discloses a method for preventing a microorganism from growing and the breakdown of urea to ammonia on the surface of skin, wall, floor, countertop or wall covering, or in absorbent materials by incorporating an effective amount of naturally-occurring and/or synthetic zeolites. The absorbent materials are diapers, clothing, bedsheets, bedpads, surgical apparel, blankets, filters, filtering aids, wall coverings, countertops, and cutting boards, etc. Use of zeolite preventing bacterial infections and rashes in mammals may compromise cell wall processes including basic transport processes. Zeolites may capture or neutralize electrons and inhibit electron transport through key enzymes of the electron transport chain such as cytochrome oxidase.

U.S. Pat. No. 6,037,057 is for a bi-component fiber in which the cross sectional area of the sheath is less than 30% of the total cross sectional area. It also discloses the use of a slickening agent and use of an anti-microbial agent which is an inert inorganic particle having a first coating with the anti-microbial properties, and a second coating which has protective properties.

One of the disadvantages of some of the prior art is that the anti-microbial additives are organic and many organic materials either act as antibiotics and the bacteria "learns" to go around the compound, or many of them give off dioxins in use.

Also, many such additives are applied topically to the fibers or fabrics and tend to wash off or wear off over time and become ineffective. Also, by washing off the additives are placed into the waste water stream.

There are many patents and other published information which are available concerning garments and other articles intended for use for incontinent persons. Many of these deal with the problem of moving body fluids away from a person's skin to prevent the type of problems created when such fluids remain in contact with the skin for long periods of time, such as rashes and other skin eruptions. Absorbent layers are provided behind the layer which touches the skin.

However, there is the danger of infection due to bacterial and fungal growth in urine-soaked fabrics and the overall discomfort caused by wet clothing.

There has been little attention to a problem which remains even when the fluids are moved away from the skin. This is the problem caused by microbes which attach to the outer layer which touches the skin even when the fluids move into the absorbent layer. These microbes cause a variety of problems.

The University of Minnesota Extension Service, Waste Education Series published an article in 1998, "Infant Diapers and Incontinence Products: Choices for Families and Communities by Gahring et al relating to this subject (hereafter "UOM Article"). This article indicates that the use of disposable diapers and incontinence products have been widely adopted for babies and for adults with certain problems. There is an estimate that there are at least ten million adult Americans who are incontinent. One of the problems is rashes and skin irritation.

Moisture absorbing incontinence products are produced in various manners including plastic film or coated nylon for a waterproof backing, paper fiber, gelling material, or cotton gauze; flannel for a middle absorbent layer and nonwoven or woven or knitted fabrics made of polyester, olefin, viscose or cotton for the coverstock.

This article discusses health issues for babies relating to the condition of the skin and to the transmission of infectious diseases. Prolonged contact with urine and stool is a major cause of diaper rash.

There are environmental problems associated with the large use of disposable products of this type. And this will increase as the number of elderly people in our society increases. While disposables are placed into landfills together with other trash, it appears that many people do not empty the contents of disposables into the toilet, and a study has shown that diaper wastes represent a significant health hazard in landfills. While many such products claim to be biodegradable, this is not always correct and there is some difficulty in making the moisture impervious layers of the plastics used in such products, biodegradable.

Also it has been found that super-absorbent disposable diapers are more effective than cloth diapers with separate waterproof pants/wraps. The transmission of infectious disease is a major concern for care, outside of the home. The fecal containment of disposable diapers is found to be significantly better than that of cloth diapers with plastic pants.

Vehicle and aircraft cabin air filters are vulnerable to the seeding of bacteria and fungi from outside air sources and air conditioning systems, thus providing hospitable sites for their inhibited growth. The latter is especially true since these filters often recirculate cooled air from air-conditioners. Thus, these materials would benefit from having antibacterial and anti-fungal agents incorporated into them. However, most prior art approaches of coating fibers or materials with anti-microbial or anti-fungal agents have limited effect.

There have been complaints about the "musty air" smell which is notices when air conditioning equipment is turned on in such cabins. This smell is caused by the growth of mold and bacteria with the air conditioning system.

There exists a need to develop fabrics and other effective material for use in air filters for vehicle and aircraft cabins that do not cause the development of resistant bacterial strains. There also still exists a need for these filters to have substrates-anti-microbial agent systems that are resistant to being washed away, thus maintaining their potency as an integral part of the filters into which they are incorporated.

U.S. Pat. No. 5,876,489, mentioned above, describes use of a cation exchange to provide a fiber bonded with silver ions, usable in a germ removing filter for sterilizing air for a sterile room such as is used in the manufacture of food products. A problem with using silver zeolite fine particles for such a filter is that the particles fall out and generate dust, thereby deteriorating the function of a HEPA filter with which it is used. When other methods are used in which the zeolite particles are two microns, with fiber filament having a diameter of 8–15 microns, insufficient zeolite particles are available on the surface of the synthetic fiber filament.

Wound care dressings can introduce pathogens that increase the danger of infection due to bacterial and fungal growth into the wound tissue because it is necessary to changing these dressings frequently. As a result of the constant re-exposure of the healing wound to the air, the dressings used to cover these wounds are suitable for the use of anti-microbial and anti-fungal fibers during their manufacture. In addition, the use of these anti-microbial materials could allow these dressings to be used for longer periods of time before they need to be changed or even to possibly be reusable, although they are usually considered disposable after one use. However, most prior art approaches of coating such fibers or fabrics with anti-microbial or anti-fungal agents have had limited success.

Burn dressings are used to prevent infection due to high potential for introducing bacteria and other pathogens into the burn tissue due to the fact that the normal protective barrier of the skin has been grossly disrupted. The possibility of bacterial and fungal growth in the burn tissue during healing is one of the major dangers to recovery. Also, as a result of the constant re-exposure of the healing burn tissue to the air during the changing of dressings, the materials used to protect these burns are suitable for the use of anti-microbial and anti-fungal fibers during their manufacture. In addition, the use of these anti-microbial materials could allow these burn dressings to be used for longer periods of time before they need to be changed.

Several patents describe anti-microbial materials in which the anti-microbial agent is resistant to being washed away. Similarly, U.S. Pat. No. 4,919,998 (1990) discloses an anti-microbial medical fabric material for use in surgical gown and scrub suits, sterilization wrappers and similar material that retains its desirable properties after repeated institutional launderings.

U.S. Pat. No. 4,226,232 discloses a wound dressing which provides many desirable properties. However, there is only brief mention of the use of anti-microbial agents, and there is no discussion of providing such agents onto the surface of the fibers contacting the wound to provide the best efficacy of anti-microbial agents.

U.S. Pat. No. 5,098,417 for a cellulosic wound dressing with an active agent ionically absorbed thereon has the anti-microbial or anti-fungal agent applied to an already prepared fabric.

U.S. Pat. No. 5,147,339 for a dressing material for the treatment of wounds has an anti-microbial applied to the already formed fabric as a coating.

U.S. Pat. No 5,219,325 for a wound dressing has a top layer and a lower layer (which contacts the wound) connected together by a fibrous layer. The lower layer has an anti-microbial applied after the layer is formed.

Thus, there still exists a need to develop metal-containing anti-microbial agents that do not cause the development of resistant bacterial strains for incorporation into fibers that are used to make a variety of materials. There also still exists a need for these anti-microbial agents to be resistant to being abraded or washed away, thus maintaining their potency as an integral part of the fibers into which they are incorporated.

PETG as used herein means an amorphous polyester of terephthalic acid and a mixture of predominately ethylene glycol and a lesser amount of 1,4-cyclohexanedimethanol. It is known that PETG can be used in polycarbonate blends to improve impact strength, transparency, processability, solvent resistance and environmental stress cracking resistance.

Udipi discloses in U.S. Pat. No. 5,104,934 and U.S. Pat. No. 5,187,230 that polymer blends consisting essentially of PC, PETG and a graft rubber composition, can be useful as thermoplastic injection molding resins.

Chen et al. in U.S. Pat. No. 5,106,897 discloses a method for improving the low temperature impact strength of a thermoplastic polyblend of PETG and SAN with no adverse effect on the polyblends clarity. The polyblends are useful in a wide variety of applications including low temperature applications.

Billovits et al. in U.S. Pat. No. 5,134,201 discloses that miscible blends of a thermoplastic methylol polyester and a linear, saturated polyester or co-polyester of aromatic dicarboxylic acid, such as PETG and PET, have improved clarity and exhibit an enhanced barrier to oxygen relative to PET and PETG.

Batdorf in U.S. Pat. No. 5,268,203 discloses a method of thermoforming thermoplastic substrates wherein an integral coating is formed on the thermoplastic substrate that is resistant to removal of the coating. The coating composition employs, in a solvent base, a pigment and a thermoplastic material compatible with the to-be-coated thermoplastic substrate. The thermoplastic material, in cooperation with the pigment, solvent and other components of the coating composition, are, after coating on the thermoplastic substrate, heated to a thermoforming temperature and the thermoplastic material is intimately fused to the thermoplastic substrate surface.

Ogoe et al. in U.S. Pat. No. 5,525,651 disclose that a blend of polycarbonate and chlorinated polyethylene has a desirable balance of impact and ignition resistance properties, and useful in the production of films, fibers, extruded sheets, multi-layer laminates, and the like.

Hanes in U.S. Pat. No. 5,756,578 discloses that a polymer blend comprising a monovinylarene/conjugated diene black copolymer, an amorphous poly(ethylene terephthalate), e.g. PETG, and a crystalline poly(ethylene terephthalate), e.g. PET, has a combination of good clarity, stiffness and toughness.

Eckart et al. in U.S. Pat. No. 5,958,539 disclose a novel thermoplastic article, typically in the form of sheet material, having a fabric comprising textile fibers embedded therein. The thermoplastic article is obtained by applying heat and pressure to a laminate comprising an upper sheet material, a fabric comprised of textile fibers and a lower sheet material. The upper and lower sheet materials are formed from a co-polyester, e.g. PETG. This thermoplastic article may be used in the construction industry as glazing for windows. One or both surface of the article may be textured during the formation of the articles.

Ellison in U.S. Pat. No. 5,985,079 discloses a flexible composite surfacing film for providing a substrate with desired surface characteristics and a method for producing this film. The film comprises a flexible temporary carrier film and a flexible transparent outer polymer clear coat layer releasably bonded to the temporary carrier film. A pigment base coat layer is adhered to the outer clear coat layer and is visible there through, and a thermo-formable backing layer is adhered to the pigmented base coat layer. The film is produced by extruding a molten transparent thermoplastic polymer and applying the polymer to a flexible temporary carrier thereby forming a continuous thin transparent film. The formed composite may be heated while the transparent thermoplastic polymer film is bonded to the flexible temporary carrier to evaporate the volatile liquid vehicle and form a pigment polymer layer. The heating step also molecularly relaxes the underlying film of transparent thermoplastic polymer to relieve any molecular orientation caused by the extrusion. Ellison also mentions that it is desirable to form the flexible temporary carrier from a material that can withstand the molten temperature of the transparent thermoplastic polymer. The preferred flexible temporary carriers used in his invention are PET and PETG.

Currently, many tee shirts, such as the grey athletic shirts, are made by blending in up to 10% of either solution dyed black polyester or stock dyed cotton. The solution dyed polyester has a disadvantage in that the product can no longer be labeled 100% cotton. The stock dyed cotton has the disadvantage in that it is not color fast, especially to bleach, and that it needs to be passed through a dye bath.

While anti-microbial agents are known in the footwear art, the agents used in these applications are generally organic substances. The disadvantage of these organic agents when used as anti-microbial agents is that bacteria can develop a resistance to their action. Thus, one is faced with the emergence of bacterial strains that are no longer affected by these anti-microbial agents which negates the function of these materials, and is harmful to humans since they are resistant to antibiotics.

One type of known shoe component is an insole disclosed in U.S. Pat. No. 4,864,740 for Disposable Insoles, which includes three layers in which the anti-microbial agent is placed into the middle layer. As an alternative, the anti-microbial can be placed into the other layers, disclosing that the particular layer into which the anti-microbial agent is used is not important.

U.S. Pat. No. 4,401,770 for Shoe Insole Having Antibacterial and Anti-fungal Properties is a flexible polyurethane foam prepared from a reaction mixture incorporating an anti-bacterial and anti-fungal agent which is a pyridinethione compound. The agent is introduced into the product and is the same concentration throughout the product.

Thus, there still exists a need to develop anti-microbial footwear components that do not cause the development of resistant bacterial strains. There also still exists a need for these components to have anti-microbial agent systems that are resistant to being worn away by abrasion, thus maintaining their potency as an integral part of the footwear components into which they are incorporated.

Sheet materials for various uses are vulnerable to the seeding of bacteria and fungi from various sources, thus providing hospitable sites for their uninhibited growth. The latter is especially true since, depending upon the end use, they often are used in environments where there is great exposure to microbes and fungi. One example is cafeteria trays. Thus, these materials would benefit from having antibacterial and anti-fungal agents incorporated onto them and/or into them. However, most prior art approaches of providing sheet materials with anti-microbial or anti-fungal agents have limited effect.

A variety of patents relate to anti-microbial materials being added to materials. For example, U.S. Pat. No. 3,959,556 (1976) relates to synthetic fibers that incorporate an anti-microbial agent. U.S. Pat. No. 4,624,679 (1986), mentioned above, uses anti-microbial agents in connection with thermoplastic materials. These materials are formed by mixing polyamide resins, anti-microbial agents, and an antioxidant for reducing the degradation of the anti-microbial agent at the high temperatures necessary for processing.

Several other patents describe anti-microbial materials in which the anti-microbial agent is resistant to being washed away. U.S. Pat. No. 4,919,998 (1990) discloses an anti-microbial material that retains its desirable properties after repeated washings.

However, these materials have two inherent commercial disadvantages. First, while the anti-microbial agents incorporated into them do show some resistance to repeated washings, these agents do leach out of the materials, primarily because they are not physically incorporated into them. In fact, in many cases, the anti-microbial agents are only loosely bound into the material and are relatively easily washed away or naturally abraded away over time.

On the other hand if the agents are buried too deeply in the material or homogeneously distributed they will not contact microbes at all and the economics of usage will be adversely affected.

Second, the anti-microbial agents used in these applications are generally organic substances. The disadvantage of these agents when used as anti-microbial agents is that bacteria can develop a resistance to their action. Thus, one is faced with the emergence of bacterial strains that are no longer affected by these anti-microbial agents which negates the function of these materials.

U.S. Pat. No. 4,923,914 for a Surface-Segregatable, Melt-Extrudable Thermoplastic Composition discloses forming a fiber or film of polymer and an additive in which the additive concentration is greater at the surface for example when surfactants are added to polymers to impart a special property thereto such as a hydrophilic character to the surface, if the additive is compatible with the polymer there is a uniform concentration of the additive throughout the polymer. In the past such webs have been bloomed to bring the surfactant to the surface. But the surfactant is incompatible at melt-extrusion temperatures. The patentee describes a process for overcoming this problem.

However, the process described has not been very usable with anti-microbial agents. For example, see U.S. Pat. No. 5,300,167 which describes the '914 patent discussed above and states that previous attempts to apply the teachings thereof to the preparation of non-woven webs having anti-microbial activity were not successful. This '167 patent provides for delayed anti-microbial activity in order to delay the segregation characteristic of the '914 patent from occurring. The additive which is used is a siloxane quaternary ammonium salt, an organic material.

While these anti-microbial agents are designed to prevent the development of resistant bacterial strains, the use of metal-containing materials presents the added difficulty of being able to successfully disperse the anti-microbial agents throughout the material. Since these metal-containing compounds exists as fairly large size particles (10 microns and greater), the ability to evenly mix or distribute them is limited. In addition, because of this size problem, these substances must necessarily be applied to the surfaces of materials instead of being incorporated into them. The latter causes the additional disadvantage of making the applied anti-microbial agents relatively labile to washings or abrasion.

Thus, there still exists a need to develop anti-microbial non-woven sheet material and fabrics for various uses that do not cause the development of resistant bacterial strains. There also still exists a need for these filters to have substrates-anti-microbial agent systems that are resistant to being washed away, thus maintaining their potency as an integral part of the filters into which they are incorporated.

U.S. Pat. No. 4,350,732 for reinforcing laminate which issued Sep. 21, 1982 discusses a moldable laminate which could be molded into curved shapes and which is bondable to a carrier surface and which is useful in the making of military boots and the like. The present invention is an improvement.

Institutional furnishings are subject to excessive wear and tear. These furnishings must withstand the constant onslaught of dirt and spills of a variety of substances. They must also stand up to frequent cleanings with industrial strength cleansers. As a result, these furnishings could be made stronger and more resistant by using anti-microbial and anti-fungal agents in their manufacture. The limited prior art approaches of coating fibers and/or fabrics with anti-microbial or anti-fungal materials have had only limited success.

Home furnishings are not subjected to as much wear and tear as institutional furnishings and are usually made of a material which has a softer "feel" and is usually more delicate than those made for institutional use. Therefore, it is difficult to make such materials which will stand up to repeated washings and to wear, particularly when they have been prepared with additives for special properties such as anti-microbial agents.

U.S. Pat. No. 3,983,061 for a process for the permanent finishing of fiber materials, including carpets, discloses an aqueous acid liquid for finishing fiber materials especially dyed carpets to make them anti-static, dirt-repellent, and optionally anti-microbial using a single bath process for finishing dyed textile floor coverings to make provide these characteristics to them. It states that the properties are "permanent" and defines this to mean retaining the properties after a "prolonged" period of wear and tear. However, the anti-microbial properties are not believed to last sufficiently long to be of commercially useful application, and the anti-microbial agent disclosed is organic in nature.

U.S. Pat. No. 4,371,577 for an anti-microbial carpet containing amino acid type surfactant is incorporated into fibrous materials prior to or after fabrication into a carpet using an organic material. The fibrous materials can be polyamide acrylic, polyester or polypropylene fibers. The preparation is accomplished in two manners. The first is that the pile yarns, the carpet foundations or the yams for carpet foundation are subjected to the impregnation treatment with a surfactant, and the other is that a carpet fabricated from fibrous materials is impregnated with an organic material.

U.S. Pat. No. 5,762,650 for a biocide plus surfactant for protecting carpets where the dyeing and anti-microbial finishing is performed simultaneously. The anti-microbial agent is an organic material.

While there are known anti-microbial agents which are said to be designed to prevent the development of resistant bacterial strains, the use of metal-containing materials presents the added difficulty of being able to successfully disperse the anti-microbial agents throughout the fibers. Since these metal-containing compounds exists as fairly large size particles (10 microns and greater), the ability to evenly mix or distribute them is limited. In addition, because of this size problem, these substances must necessarily be applied to the fibers instead of being incorporated into them. The latter causes the additional disadvantage of making the applied anti-microbial agents relatively labile to washings.

Thus, there still exists a need to develop fabrics, materials and surfaces substrates for use in home and institutional furnishings which contain metal-containing anti-microbial agents that do not cause the development of resistant bacterial strains for incorporation into fibers that are used to make a variety of fabrics. There also still exists a need for these anti-microbial agents to be resistant to being washed away, thus maintaining their potency as an integral part of the fibers, fabrics, materials, and furnishings into which they are incorporated.

Medical wipes are used for a variety of cleaning and disinfectant purposes in hospital and other institutional settings. Even though most current materials of this kind are disposable, their use increases the potential of moving pathogens from surface to surface. Any spreading of these pathogens increases the possibility of bacterial and fungal growth on a variety of surfaces, which can lead to the transmission of infectious materials, particularly in institutional settings. Thus, the materials used in medical wipes are amenable to the incorporation of anti-microbial and anti-fungal fibers during their manufacture. By using these anti-microbial materials, medical wipes could be used for longer periods of time before they need to be changed. However, most prior art approaches of coating fibers or fabrics with anti-microbial or anti-fungal agents have had limited success.

U.S. Pat. No. 5,709,870 (1998), mentioned above, discloses a silver-containing anti-microbial agent that has good affinity to the fiber and is stable to heat and light. The anti-microbial consists of silver bound to carboxymethyl-cellulose in the amount of 0.01 to 1.0 percent silver by weight that is applied to the fibers.

While these anti-microbial agents are designed to prevent the development of resistant bacterial strains, the use of metal-containing materials presents the added difficulty of being able to successfully disperse the anti-microbial agents throughout the fibers. Since these metal-containing compounds exists as fairly large size particles (10 microns and greater), the ability to evenly mix or distribute them is limited. In addition, because of this size problem, these substances must necessarily be applied to the fibers instead of being incorporated into them. The latter causes the additional disadvantage of making the applied anti-microbial agents relatively labile to washings.

Thus, there still exists a need to develop metal-containing anti-microbial agents that do not cause the development of resistant bacterial strains for incorporation into fibers that are used to make a variety of materials. There also still exists a need for these anti-microbial agents to be resistant to being abraded away, thus maintaining their potency as an integral part of the fibers into which they are incorporated. In the event they are not disposable, they need to be resistant to washings.

SUMMARY OF THE INVENTION

It is an object of the present invention to provide an anti-microbial fiber in which the anti-microbial agents are efficacious and adhere to the fiber and are greatly resistant to washing off or wearing off of the fiber or fabric to which they are applied.

It is also an object of the present invention to provide an anti-microbial fiber in which the anti-microbial additives are inorganic.

It is another object of the present invention to provide a fiber with anti-microbial properties in which the anti-microbial agent is applied to certain areas, or has higher concentrations in certain areas, to reduce the amount of the anti-microbial agent which needs to be used and thus lower the cost of such fiber and/or a fabric including such fiber.

It is another object of the present invention to provide an anti-microbial fiber combined with non-anti-microbial fibers for use in anti-microbial finished fabrics that are able to withstand significant wear and washings and still maintain their effectiveness.

It is a further object of the present invention to provide an anti-microbial fiber:

combined with color pigments for coloration for the use in anti-microbial finished fabrics to withstand fading;

combined with UV additives to withstand fading and degradation in fabrics exposed to significant UV light;

combined with additives to make the surface of the fiber hydrophilic or hydrophobic;

combined with additives to make the fabric flame retardant or flame resistant;

combined with additives to make the fabric anti-stain; and/or using pigments with the anti-microbial so that the need for conventional dyeing and disposal of dye materials is avoided.

These and other objects of the present invention are accomplished by synthetic fibers having anti-microbial and/or anti-fungal properties using various thermoplastic polymers blended with other types of fibers, and additives, some incorporating natural fibers.

Thus, the present invention provides a synthetic anti-microbial fiber comprising high and low levels of various thermoplastic polymers and controlled concentrations of inorganic anti-microbial additives mixed with polymers and selectively placed in the end product for greatest technical effectiveness and cost effectiveness.

The anti-microbial and/or other agent(s) are held in the sheath and are exposed externally by suitable sizing of particle cubes and sheath thickness, e.g., using one micron cubes and 2 micron thick sheaths, and similar ratios of sheath to core in other sizes.

The present invention also provides a synthetic anti-microbial fiber comprising high tenacity polymers e.g. polyesters, polyethylene terephalate (PET) in one portion and hydrolysis resistance polymers in another portion with hydrophilic and anti-microbial additives. In some applications the latter portion can be deliberately made hydrolysis-vulnerable to allow "blooming" and enhanced access to anti-microbial additives in the course of several washings or extended uses.

Also, the present invention provides an anti-microbial finished fabric by blending the synthetic anti-microbial fibers with non-anti-microbial fibers such as cotton, wool, polyester, acrylic, nylon, and the like.

The various polymers, include but are not limited to, polyethylene (PE), polypropylene (PP), polyethylene terephthalate (PET), PCT, PETG [PET, type G], Co-PET and copolyesters generally, Styrene, polytrimethylene terephalate (PTT)m 3 GT, Halar®, polyamide 6 or 6,6, etc. The additives include pigments, hydrophilic or hydrophobic additives, anti-odor additives and anti-microbial/anti-fungal inorganic compounds, such as copper, zinc, tin and silver.

PETG is an amorphous binder fiber which can be blended into yarns with other fibers to form fabrics, as well as non-woven fabrics. After heat activation, the PETG fiber melts, wets the surface of the surrounding fibers, and settles at the crossing points of the fibers, thus forming "a drop of glue" which bonds the fibers together and distributes the anti-microbial additives.

The excellent wetting characteristics of PETG can be used to distribute the anti-microbial additive uniformly within a yarn or fabric. In addition to the zeolite of silver, the PETG could carry other inorganic anti-microbial additives such as copper, zinc, or tin.

In addition to the anti-microbial component, the invention may be used to carry pigments with the PETG to achieve certain colors without the need to dye the other fibers.

The created synthetic fibers of polymers and additives can further be blended with non anti-microbial fibers to provide anti-microbial finished fabrics that are able to withstand significant wear and washings and maintain their effectiveness.

The use of hot water improves the products in that washing the fibers/products in hot water opens the pores of the PET and such washed products perform better than unwashed products (this is thought to be due to the removal of spinning/weaving lubricants).

Material can be made in biodegradable form, such as by adding corn starch to the core or sheath polymers. This enables whole families of disposable fibers and fabrics.

Use of a cloth diaper and a garment over it is effective, especially when anti-microbial/anti-fungal fibers are used for the fibers which have contact with the waste matter, although beneficial effects are available even when the antimicrobial/anti-fungal agents are used only in the fibers which touch the body.

Due to the urine soaking which occurs with incontinent persons, these garments are suitable for the use of anti-microbial and anti-fungal fibers during their manufacture. The use of such anti-microbial material allows these garments to be reusable without the negative effects of present reusable garments of this type. The anti-microbial may be fabric (knitted or woven) plus absorbent pads. This also applies to bed packs for bed ridden patents to prevent bed sores.

It is an object of the incontinent garment embodiment to provide garments and articles intended for use for incontinent persons which articles have anti-microbial and/or anti-fungal fibers in a woven or non-woven fabric of the garment or article which is in contact with such person's skin to eliminate or substantially reduce the problems caused by such microbes.

It is another object of the incontinent garment embodiment to provide such garments and articles which may be cleaned and reused many times while maintaining the beneficial anti-microbial qualities thereof.

It is a further object of the incontinent garment embodiment to provide anti-microbial fibers in the absorbent material usually used in such articles.

Thus, there still exists a need to develop garments and articles of the type described which are made of fibers having metal-containing anti-microbials that do not cause the development of resistant bacterial strains for incorporation into fibers that are used to make a variety of fabrics. There also still exists a need for these anti-microbial agents to be resistant to being washed away, thus maintaining their potency as an integral part of the garments and articles into which they are incorporated.

It is a principal object of the air filter embodiment to provide vehicle and aircraft cabin air filter materials that meet these needs in a manner consistent with industry specifications, overall durability, and cost-effectiveness.

It is another object of the air filter embodiment to provide such filters which are effective to eliminate or at least substantially reduce the "musty air" smell noticed in such cabins.

The foregoing objects are met by filters based on anti-microbial fibers that have been designed using inorganic silver-containing compounds that allow the formation of both mono- and multi-component polymeric fibers having these anti-microbial agents intermixed within the polymer during fiber formation. The concentration of the anti-microbial agent can be varied within each individual fiber as a gradient using mixing strategies and also from fiber to fiber. The concentration of anti-microbial agent within a fabric or material made from these anti-microbial fibers can also be varied regionally using fibers containing varying amounts of anti-microbial agents in conjunction with both natural and synthetic fibers having different amounts of anti-microbial agents or even no added anti-microbial agents. A variety of other agents can be added, either by mixing or topically, to color the fibers and/or to make it resistant to staining, fire, and ultraviolet (UV) light as well as altering its water absorbing qualities. Various polymers, without limitation, can be used to form these fibers. In the context of this invention, anti-microbial refers, but is not limited, to antibacterial and anti-fungal.;

It is an object of the wound and burn dressings embodiment to provide wound care dressings that meet these needs with attendant durability and comfort in a cost-effective manner.

It is another object of the wound and burn dressings embodiment to provide wound care dressings that are one time use products having durability and workability.

A further object of the wound and burn dressings embodiment is to provide such dressings in which the anti-microbial agent is available at the surface of the fibers.

It is the object of the wound and burn dressings embodiment to provide burn dressings that meet these needs with substantial durability and comfort in a cost-effective manner.

Still a further object is to provide a dressing which is useful by itself, or in combination with other wound dressing systems to add fibers to such a system which are in direct or near contact with the wound to provide anti-microbial agents on the surface of the fibers closest to the wound.

Yet a further object of the wound and burn dressings [invention] embodiment is to provide such a dressing which maintains its vigor even after any liquid or cream anti-microbial agents that may be used therewith have lost their efficacy or have left the dressing and wound due to movement of the patent and the dressing itself.

The foregoing objects are met by wound care and burn dressings based on anti-microbial fibers that have been designed using inorganic silver-containing compounds that allow the formation of both mono- and multi-component polymeric fibers having these anti-microbial agents intermixed within the polymer during fiber formation. The concentration of the anti-microbial agent can be varied within each individual fiber as a gradient using mixing strategies and also from fiber to fiber. The concentration of anti-microbial agent within a fabric or material made from these anti-microbial fibers can also be varied regionally using fibers containing varying amounts of anti-microbial agents in conjunction with both natural and synthetic fibers having different amounts of anti-microbial agents or even no added anti-microbial agents. A variety of other agents can be added, either by mixing or topically, to color the fibers and/or to make it resistant to staining, fire, and ultraviolet (UV) light as well as altering its water absorbing qualities. Various polymers, without limitation, can be used to form these fibers. In the context of this invention, anti-microbial refers, but is not limited, to antibacterial and anti-fungal.

FIG. 10 shows a wound care dressing 52 which includes a bottom layer 46, a top layer 48 and an intermediate absorbent fibrous layer 50 which joins the other two layers. The bottom layer 46 is used directly against the wound and therefore the fibers of this layer have the anti-microbial agent applied thereto as described below.

The invention uses fibers with silver zeolite as a component in a wound dressing pad. The finished product may be either the pad itself or, the pad combined to PVC, adhesive or other materials. The wound dressing pad may be woven, knit, non-woven or other fabric type and may contain any variety of natural or synthetic fibers in addition to the anti-microbial fibers. The pad may or may not have a cover stock over it, as well as other medicated treatments.

The purpose is to help prevent the growth of microbes in/on a wound care dressing, as well as the wound area, as it heals. The theory here is that a reduction in microbes/bacteria will facilitate healing and minimize the potential for infections.

Infections are a significant concern with wound care and bum care. body fluids at the wound on bum site provide both the "food" and moisture for GHC microbial growth.

A dressing media containing an anti-microbial additive would prevent the growth of microbes in the media in contact with the wound or bum. This may allow the dressing to remain in place longer and reduce the trauma when a "dressing is changed."

It is one object of the fabric embodiment to provide a fiber which is used to form a fabric to which qualities may be imparted which last for the life of the fabric.

It is another object of the fabric embodiment to provide such a fabric which is provided with coloring which remains fast even to sunlight and many launderings.

It is a further object of the fabric embodiment to provide such a fabric which is provided with a colorant without the use of a dye bath.

It is still another object of the fabric embodiment to provide a fiber and fabric of the type described which possesses anti-microbial properties.

It is yet another object of the fabric embodiment to provide a fiber and fabric of the type described in which characteristics may be imparted using agents which become permanently fixed and are maintained for the life of the fabric.

These objects and others are accomplished in accordance with the present invention which uses PETG:

As a carrier for pigments for coloration for use in finished fabrics to withstand fading;

With pigments together with other fibers, so that the need for conventional dyeing and disposal of dye materials is avoided;

With pigments and other fibers, and the resulting fabric possesses excellent fastness for both sunlight resistance and washing;

With pigments for coloration, the color of the fabric remains fast for in excess of 50 commercial launderings;

With pigments blended with cotton, which leaves the encapsulated pigment attached to the outside of the cotton fiber and ceases to be a fiber after activation, so that the resulting fabric can still be labeled 100% cotton fiber; and With anti-microbial and/or other additives with any natural fibers, so that the resulting fabrics have anti-microbial and/or other properties with the same characteristics of natural fabrics.

PETG may be used as one of the polymer blends and/or carriers for a wide variety of applications. PETG is an amorphous binder fiber that can be blended into yarns with other fibers to form woven fabrics, as well as knits and non-woven fabrics. It has two characteristics of particular interest: (1) excellent wetting and (2) low melting temperature (which can be controlled between 90° C. and 160° C.). It is used in the present invention as a carrier to carry pigments and/or anti-microbial additives and/or other additives and is blended with other fibers which may be natural fibers such as cotton, silk, flax, wool, etc. or other synthetic fibers such as: PET, PP, PE, Nylon, Acrylic, etc. After heat activation, the PETG melts, continuously releases the color pigments and/or anti-microbial or other additives and wets the surface of the surrounding fibers with the pigment and/or anti-microbial or other additives it carries. It settles at the crossing points of the fibers, thus forming "a drop of glue" which bonds the fibers together. Therefore, PETG delivers and distributes the pigments and/or anti-microbial or other additives uniformly within a fabric, generating the finished fabrics and/or fabrics having anti-microbial properties.

Since the natural fibers used to blend with PETG are not changed physically after heat activation of PETG, they contain the same characteristics as natural fibers. The PETG may be used together with or without anti-microbial agents to form a fabric having excellent color fastness even in the presence of sunlight, and will withstand many washings without deterioration. The fabric is made by blending PETG used as a carrier for pigments and/or anti-microbial additives, with cotton or any other fibers of synthetic material such as from polyester and rayon, and activating PETG from 110° to 140° C. The color is thus provided to the yarn and fabric without the need of going through a dye bath. This fabric remains color-fast for in excess of 50 commercial launderings.

The excellent wetting characteristics of PETG can be used to distribute the pigments and/or anti-microbial additive uniformly within a yam or fabric. While many anti-microbial agents may be used, such as those, which use copper, zinc, or tin, the preferred agent is zeolite of silver. In addition to the anti-microbial component and the pigment added to the PETG, the PETG may be used as a carrier to add other properties to yam and fabric, such as fire retardants.

It is a principal object of the footwear components embodiment to provide such footwear components that meet these needs in a manner consistent with industry specifications, overall durability, and cost-effectiveness.

It is another object of the footwear components embodiment to provide such footwear components in various forms such as rigid, semi-rigid or flexible and which may be constructed using fibers or not as desired.

A further object of the footwear components embodiment is to have the anti-microbial agent as close as possible to a person's foot.

An additional object of the footwear components embodiment is to have a higher concentration of the anti-microbial and/or anti-fungal agent close to the surface and not wasted by being placed into other parts of the where the anti-microbial property is not needed.

The foregoing objects are met by footwear components such as insoles, midsoles, box toes, counter and linings of footwear products, e.g., shoes, slippers, sneakers and the like in which the anti-microbial agent is available for the life of the product and not washed away or worn away by sweat or abrasion. Also, the anti-microbial agent is placed into the component close to or on the surface which is most needy of the protection, such as the part of an insole closest to the foot of a user when the insole, or other component is assembled into a footwear product. Thus, the fungi or microbes which may form and create odors or other problems are killed on contact with the surface of the shoe component anti-microbial surface area.

The footwear component of the disclosed products can be a nonwoven fabric of synthetic fibers, primarily polyester, but which could be acrylic, nylon, rayon, acetate, PP, and the like. The fabric can have a weight from 65–400 grams per square meter and typical fibers range from 1.2 dTex to 17 dTex with a cut length of 15–180 mm. They are carded, cross-lapped and needle punched, but could be produced on other types of nonwoven equipment, such as spun laced or spun bonded equipment.

The impregnation is a latex of SBR, vinyl acetate, PVC, acrylonitrile, and the like. Impregnation is from 1–4 times the weight of the nonwoven fabric on a dry basis. A range of fillers such as clay, calcium carbonate, and the like are used to reduce the cost. There are two basic methods. One is to mix the anti-microbial with latex compound and impregnate it into the insole. The other is to use anti-microbial fibers on the insole in various manners.

It is a principal object of the present film embodiment to provide such sheet and film materials that meet these needs in a manner consistent with industry specifications, overall durability, and cost-effectiveness.

It is another object of the film and sheet embodiment [present invention] to provide such sheet materials in various forms such as rigid, semi-rigid or flexible and which may be constructed covered with thin films, or not, as desired.

The foregoing objects are met by sheet and film materials of an anti-microbial non-fibrous material such as melted thermoplastic material that has been designed using inorganic silver-containing compounds that allow the formation of both mono- and multi-layer polymeric materials having these anti-microbial agents intermixed within the polymer during material formation.

The anti-microbial will usually be included at and near the surface of a thin layer such as a film. The concentration of the anti-microbial agent can be varied as a gradient using mixing strategies. The concentration of anti-microbial agent within or on the surface of sheet material can also be varied regionally using materials containing varying amounts of anti-microbial agents in conjunction with both natural and synthetic materials having different amounts of anti-microbial agents or even no added anti-microbial agents. A variety of other agents can be added, either by mixing or topically, to color the material and/or to make it resistant to staining, fire, and ultraviolet (UV) light as well as altering its water absorbing qualities. Various polymers, without limitation, can be used to form these fibers. In the context of this invention, anti-microbial refers, but is not limited, to antibacterial and anti-fungal.

The present invention provides several embodiments, one of which relates to the co-extrusion of flat or shaped films or profiles. The product may be a multi-layer construction with the surface layer, on one or both sides, containing zeolite of silver (or other metal such as tin, copper, zinc, etc.).

The product may be a flat film for use in a flat form for counter tops, floors, walls, or molded into shapes such as cafeteria trays, serving dishes, high chair table, refrigerator trays, microwave liners, and luggage.

As a profile the extrusion may be a rain gutter, a screen enclosure, a counter top, hand railing, duct work, sanitary piping, water pipe, gasket materials, around dishwasher, garage door), etc.

The same concept applies to multi-layer injection molded parts. In this case the surface layer may have anti-microbial properties in applications such as telephone handsets, baby bottles, computer keyboards, plastic utensils, and milk bottles.

The choice of particle size of the zeolite is based on the thickness of the film to obtain the best combination of surface area with anchoring in the film. For example, a very thin film of $3\mu$ would be best served with a $1-2\mu$ zeolite, which would have a maximum dimension of $2\times 1.73$ or about $3.5\mu$.

The inner films could be made of basically any thermoplastic resin, such as; PE, PP, PET, PS, PCT, Polyamide (nylon), Acrylic, PVC, etc. The surface layer(s) could be made of the same polymers plus some low temperature ones such as PETG, Polycaprolactone, EVA, etc.

It is a principal object of the present embodiment to provide such sheet and film materials that meet these needs in a manner consistent with industry specifications, overall durability, and cost-effectiveness.

The foregoing objects are met by sheet and film materials of an anti-microbial non-fibrous material such as melted thermoplastic material that has been designed Home and institutional furnishings are provided which are made from fibers, yarns, fabrics, materials, and substrates having anti-microbial properties using inorganic silver-containing compounds. This allows, for example, the formation of both mono- and multi-component polymeric fibers having these anti-microbial agents intermixed within the polymer during fiber formation. The concentration of the anti-microbial agent can be varied within each individual fiber as a gradient using mixing strategies and also from fiber to fiber. The concentration of anti-microbial agent within a fabric or material made from these anti-microbial fibers can also be varied regionally using fibers containing varying amounts of anti-microbial agents in conjunction with both natural and synthetic fibers having different amounts of anti-microbial agents or even no added anti-microbial agents. A variety of other agents can be added, either by mixing or topically, to color the fibers and/or to make it resistant to stains, fire, and ultraviolet (UV) light, as well as altering its water absorbing qualities. Various polymers, can be used to form these fibers. In the context of this invention, anti-microbial refers, but is not limited, to having anti-bacterial and anti-fungal properties.

It is the object of the present medical wipes embodiment to provide medical and health care wipes that meet these needs with attendant durability in a cost-effective manner.

It is another object of the present embodiment to provide medical and health care wipes that which have anti-microbial properties and which will not be abraded away by use.

The foregoing objects are met by medical wipes based anti-microbial fibers that have been designed using inorganic silver-containing compounds that allow the formation of both mono- and multi-component polymeric fibers having these anti-microbial agents intermixed within the polymer during fiber formation.

Medical or health care wipes of the present embodiment have a variety of purposes. One is to absorb fluid or semi-fluid body substances such as blood. Another is to provide a liquid or semi-liquid for cleaning and/or disinfecting an area of the body. A further one is to disinfect or clean instruments of various types which are used in the medical field in and around the human body. The actual construction of such wipes differ depending upon the intended use.

However, there are some similarities in many such wipes. They are made from non-woven materials and have an active surface which is liquid permeable, a thicker under layer of an absorbent material, and an upper layer of liquid impervious material so that a user of such a wipe will not have the liquid touch the users fingers, which are thus protected. For convenience some types will have a handle. If the wipe is to absorb liquid materials, the absorbent material will be dry. However, if the wipe is used for cleaning purposes, the absorbent material will usually be the reservoir for the liquid or semi-liquid cleaning material.

In each type of wipe, at least the surface of non-woven material which engages the skin or material to be cleansed is provided with anti-microbial properties as described herein. That is an inorganic anti-microbial agent is incorporated into the outer surface layers of its fibers to provide anti-microbial properties thereto.

The concentration of the anti-microbial agent can be varied within each individual fiber as a gradient using mixing strategies and also from fiber to fiber. The concentration of anti-microbial agent within a fabric or material made from these anti-microbial fibers can also be varied regionally using fibers containing varying amounts of anti-microbial agents in conjunction with both natural and synthetic fibers having different amounts of anti-microbial agents. A variety of other agents can be added, either by mixing or topically, for different reasons, such as altering its water absorbing qualities. Various polymers can be used to form these fibers. In the context of this invention, anti-microbial refers, but is not limited, to anti-bacterial and anti-fungal.

The invention uses fibers with silver zeolite as a component in a medical wipe cloth. The finished product may be constructed of non-woven, knit, woven or other material. It may also be treated or pre-moistened with a topical treatment such as a soap solution or other additive. The finished product may be produced from any combination of natural or synthetic fibers in addition to the anti-microbial fibers. A wipe cloth may be unitary or combined or laminated to some other fabric.

The purpose of this invention is to help prevent the growth and spread of microbes/bacteria when a wash cloth or wipe comes in contact with the human body. Without the anti-microbial treatment, the wash cloth or wipe merely spreads bacteria. With the anti-microbial treatment, it is believed that bacteria are killed from contact with the anti-microbial treated wash cloth or wipe.

Many current wipe cloths used in food service or the home collect bits of organic matter which does not fully rinse out. This matter becomes a food source for the growth of bacteria and mold.

This invention incorporates an anti-microbial additive, e.g. zeolite of silver, in fiber used to make wipes for food service.

The healthcare wipe currently has preservatives added to the liquid in the packages so that the wet wipe will not contain bacteria or mold. Preservatives by their nature can cause allergic reactions when they come in contact with the skin.

Other objects, features and advantages will be apparent from the following detailed description of preferred embodiments taken in conjunction with the accompanying drawings in which:

BRIEF DESCRIPTION OF THE DRAWINGS

FIGS. 1A, 1B, 1B', 1B" and 1C are cross-sectional views of various fiber configurations used in practice of the various embodiments of the invention.

FIG. 2 is a sketch of a fibrous mass using one or more of the fibers of FIGS. 1A–1C.

FIG. 27 is a cross-sectional exploded view through an office partition.

FIG. 28 is a schematic view of a humidifier evaporation surface media used to humidify air.

DESCRIPTION OF PREFERRED EMBODIMENTS OF THE INVENTION

Figure 4:
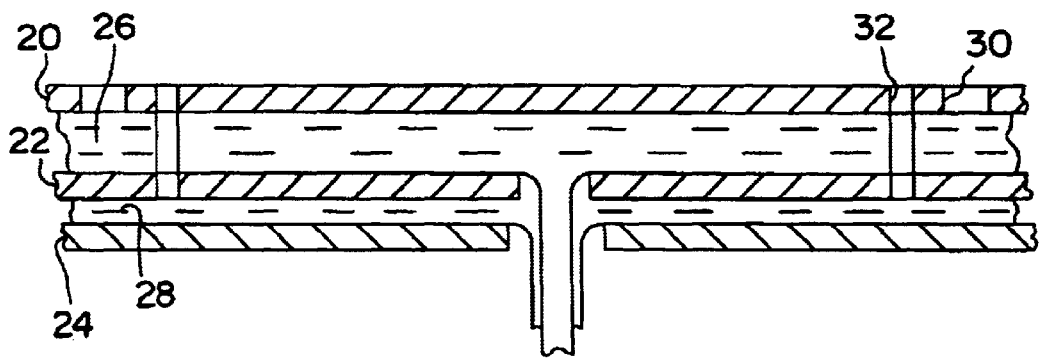
FIG. 4 is a sectional view through the exit of the extruder showing the formation of coaxial bi-component fibers of the present invention.

In the United States, all claims concerning anti-microbial and anti-properties properties must be thoroughly tested to Environmental Protection Agency (EPA) and Food and Drug Administration (FDA) standards before making claims. The anti-microbial herein can be said to "kill bacteria" in that it kills 99.99% (log 4) of bacteria in 24 hours, and "anti-microbial" in that is kills 99.9% (log 3) of bacteria in 24 hours. This is based upon actual test results. Testing, such as by using the shake flask test, has demonstrated that when fibers and fabrics are tested using the anti-microbial system disclosed herein, the number of bacteria on the fibers is reduced by 99.99% or more over a 24-hour period and at least by 99.9%. This testing was performed using several different bacteria, including Pseudomonas aeruginosa, Staphylococcus aereus and Klebsiella pneumoniae. The testing was conducted using both unwashed fibers and fibers that had been washed fifty times to simulate use of the fiber in an application, such as a pillow. The EPA has indicated that products tested using this system may claim "Prohibits Bacteria Growth and Migration Along the Surface of the Product." The addition of the agent in this system inhibits the growth of mold and mildew or odor-causing bacteria in the fibers. This is a true anti-microbial product. The fibers retain their efficacy after simulated use conditions so that the anti-microbial action lasts the life of the product.

THE FIBERS AND THE ADDITIVES

According to a first configuration of the present invention shown in FIGS. 1A–2 a bi-component fiber 10A is formed of a sheath component S and a core component C using polyethylene terephthalate (PET) (or other thermoplastic polymer) in the core, making up between 20 to 80% of the fiber by weight. The sheath is also PET, or other thermoplastic polymer, making up between 80 to 20% of the fiber by weight including, as a dispersed solid, additive A (or compounded with the sheath plastic) an anti-microbial compound, to gain the efficiency of the additive on the surface and not wasting the additive in the core.

In the more generalized case as mentioned above, the sheath may be quite thin. However, preferably the sheath is more than 30% of the total fiber cross-section. It has been found that one of the best methods for retaining the anti-microbial qualities in the fiber and in fabrics is to use sheath thicknesses which are properly related to the size of the anti-microbial additive particles. For example, when the anti-microbial particles are approximately 1 micron cubes, which provides diagonal dimensions of approximately 1.7 microns, the sheath thickness would be in the vicinity of 2 microns. In this manner the particles of the agent are firmly held in the sheath by the material of the sheath holding them in place. When the particles are larger or smaller, the thickness of the sheath is adjusted accordingly.

The anti-microbial/anti-fungal additives are inorganic compounds using such metals as: copper, zinc, tin, and silver. The best results are obtained using a zeolite of silver dispersed in a polyethylene (PE), PET, or polybutylene terephthalate (PBT) carrier, but could be added directly to a melt of a sheath thermoplastic without an intermediate carrier. The total anti-microbial additive ranges from 0.2% (0.002) to 6.0% (0.06) by weight of fiber depending on performance requirements. The anti-microbial additives are held in the sheath and are prevented from washing off over time and remain effective, especially when the sheath-thickness to agent-particle size ratio is in a desirable range as mentioned above and discussed in more detail below.

The bi-component anti-microbial/anti-fungal synthetic fiber size would preferably range from 0.7 dTex to 25.0 dTex and could be produced as a cut staple fiber in lengths from 1.0 mm to 180 mm, or in a continuous filament.

Additives which can be incorporated include one or more of UV stabilizers at 0.1% (all %'s herein are by weight unless otherwise stated) to 5.0%; fire retardant (FR) additives at 0.1% to 5.0%; pigments at 0.1% to 6.0%; hydrophilic additives at 0.2% to 5.0%; hydrophobic additives at 0.2% to 5.0%; and/or anti-stain additives at 0.2% to 5.0%.

A second configuration of this first embodiment of the present invention is a bi-component fiber 10B in which the components x, y (x=strength, y=functional portion) are side-by-side and the same polymers and additives are used as described above. Variants of this are shown in FIG. 1B' in which the tri-component fiber 10B' has components x1, x2 and y', and in FIG. 1B" in which the four-component fiber 10B" has components x1, x2, y1 and y2.

A third configuration shown in FIG. 1C is a continuous filament 10C that could be used by itself as the binder or as part of a yarn or fabric with cooperating (strength) fibers indicated at 10D.

It should be understood that the nominal "binder" fiber or binder component can also be a strength enhancer in some combinations. It will also be understood that other variants with respect to FIGS. 1A–1C, including, but not limited to combinations, can be made. For example, a first extrusion could produce intermediate fiber products as in FIG. 1A and such products could be put together with each other or separate strength fibers and processed to produce simulations of FIGS. 1B, 1B', 1B", 1C.

FIG. 2 shows a non-woven or woven fibrous mass M made up of any of the fibrous configurations of FIGS. 1A–1C after heating wherein the binder fiber component melts and flows to form locking knots at many (if not most or all) of the cross-over points or nodes N of the fibrous mass to enhance strength and durability of the mass while maintaining a dispersion of the binder materials and its functional additive(s).

While the preferred embodiment is a PET/PET bi-component with zeolite of silver being used only in the sheath. Resins with different viscosities can be used to obtain improved performance. A PCT/PET arrangement is one variation which takes advantage of the hydrolysis resistance and resilience; however, the PET/PET is more cost effective, especially for use in apparel and bedding.

FIGS. 1A–2 can also be used to describe a second embodiment grouping of practice of the invention.

The first configuration of the second embodiment of the present invention is a bi-component fiber of a core and a sheath as shown in FIG. 1A using PET or other high tenacity polymer in the core at between 20% and 80% by weight of the fiber. Poly 1,4 cyclohexylene dimethylene terephthalate (PCT) or other hydrolysis resistant polymer is used for the sheath at 80% to 20%. The core is designed to provide the strength of the fiber and the modulus can be varied to create a high modulus fiber with properties of high tenacity and low elongation similar to cotton, or a low tenacity and higher elongation fiber with properties similar to wool; or anywhere in between to obtain different fibers to make them as compatible as possible for their end uses and for any blend in which they will be used. In fibers, modulus refers to the area under the curve in a stress/strain curve. The sheath is preferably over 30% of the total cross sectional area. The sheath uses PCT which provides a hydrolysis resistant surface with good wrinkle resistance and resistance to long term washings in boiling water and strong soaps.

Additives in this second embodiment include pigments, compounds to create a hydrophilic surface, and anti-microbial, anti-fungal, anti-odor additives. The pigment additives are to provide uniform colors that do not fade significantly over long-term use and washing, unlike dyes. Compounds may be used which create a hydrophilic surface and this is designed to wick body moisture away from the skin and evaporate to create comfort for a wearer of a garment containing such fibers and is particularly useful for career apparel such as uniforms, work clothes, etc. The anti-microbial, anti-fungus and anti-odor additives can be varied depending on the functionality of the career apparel.

The bi-component anti-microbial/anti-fungal synthetic fiber size ranges from 0.7 dTex to 25.0 dTex and can be produced as a cut staple fiber in lengths from 1.0 mm to 180 mm, or in a continuous filament.

Another arrangement (FIG. 1C) is a bi-component continuous filament that could be used by itself or as part of a yarn or fabric.

FIGS. 1A–2 can also be used to describe a third embodiment grouping of practice of the invention.

The third embodiment of the invention is a mono-component of homo-polymer fiber made from low temperature polymers with a melting or softening temperature below 225° C. such as PETG. It relates to a binder fiber carrier for anti-microbial additives, which can be further blended with non-anti-microbial fibers to provide an anti-microbial finished fabric that is able to withstand significant wear and washings and maintain their effectiveness. The anti-microbial additives are inorganic.

A mono-component or homo-polymer fiber used in this embodiment was made from low temperature polymers with a melting or softening temperature below 225° C. such as PETG (PET modified with 1,4, cyclohexanedimthanol), PE, PP, co-PET, or amorphous PET. Another low melting temperature polymer which may be used is polycaprolactam (PCL). The anti-microbial additives are inorganic compounds made from metals such as copper, tin, zinc, silver, etc. The preferred compound is a zeolite of silver dispersed in PE, PET, or PBT before being added to the fiber. The additives could be added directly to the primary polymer with pre-dispersion. The total active ingredients range from 0.1 to 20% by fiber weight. Other inorganic metals such as tin, copper, zinc, etc. work also but not as well as zeolite of silver.

The binder (carrier) fiber containing polymers and anti-microbial additives can be blended with non anti-microbial natural fibers such as cotton and wool, or synthetic fibers such as polyester, acrylic, nylon, PTT, 3GT, rayon, modified rayon, and acetate to an anti-microbial finished fabrics that is able to withstand significant wear and washings and maintain their effectiveness.

A typical example is a fiber using the PETG polymer with the zeolitic contained silver additive blended with cotton up to 10% by weight to produce a bed sheet. The binder fiber is activated in the drying cycle of the final bleaching operation or other heat operation. The PETG melts and wets the surface of the cotton fibers to carry the anti-microbial characteristics to the entire sheet with an added benefit of increasing strength and reducing pilling.

The fiber size ranges from 0.7 dTex to 25 dTex and a staple length of 1.0 mm to 180 mm. A continuous filament yarn can also be produced that can be used in a wrap spun application whereby non-anti-microbial fibers are spun around the anti-microbial filament.

The antimicrobial product withstands more than 50 commercial washings at 80° C. and/or dry cleanings. It is immune to UV exposure of at least 225 kj. It possesses excellent abrasion resistance and is unaffected by tests such as Tabor or Wyzenbeek.

The present invention also provides a unique way to use polymers such as PETG to carry and deliver anti-microbial additives and/or pigments to a natural non-anti-microbial fiber, such as cotton, wool, possibly mixed with polyester, nylon and the like, and generate a final binding fabric having anti-microbial properties.

PETG has two characteristics of interest: (1) excellent wetting and (2) low melting temperature. In the present invention, it is used as a carrier to carry anti-microbial additives and be blended with non-anti-microbial fibers. After heat activation, the PETG melts, continuously releases the anti-microbial additives and wets the surface of the surrounding non anti-microbial fibers with the anti-microbial additives it carries. Thus, PETG delivers and distributes the anti-microbial additive uniformly within a fabric and the PETG holds the anti-microbial agent in place, generating the finished fabrics having anti-microbial property. Since the natural fibers used to blend with PETG are not changed physically in this process, they contain the same characteristics as natural fibers.

The bi-component fiber may be formed by the use of pellets of the two different polymers or a direct polymer stream from the reactor of which the fiber is to be formed. The arrangement shown in FIG. 1A is intended for a configuration of a core fiber, and a sheath fiber which contains an additive, e.g., an anti-microbial agent. Since the best of the anti-microbial agents known at this time to the present inventor is zeolite of silver, the present example uses this agent. The intent is to use the minimum amount necessary to provide the desired characteristics. The additive provides the desired anti-microbial effect only at the surface. Therefore, if the bulk of the additive is located within the volume of the fiber well below the surface, that portion will not be useful for most or all of the life of the material into which the fiber is made. Since there frequently is some surface abrasion, some of the additive particles which are just below the surface when the fiber is made, become available at the surface, later in the life of the product.

In the past, attempts have been made to provide the additive at the surface, and the result was that the additive particles did not have a very useful life since they were removed from the surface by washing and wear or use. Therefore, the present invention strongly attaches the additive particles to the outer region of the fiber.

It has been possible to make particles of zeolite of silver as small as 1 micron cubes. A particle of such size will have a diagonal dimension of about 1.7 micron. Therefore, the smallest thickness of the sheath would be about 2 microns. The present invention permits a core/sheath arrangement in which the sheath is as small as 2 microns in thickness with the additive incorporated into the sheath. The diameter of the sheath is adjusted to the particle size so that the particles are held firmly in place and are available at the surface of the sheath. The particles may be smaller or larger than 1 micron cubes or larger, and the sheath may be correspondingly smaller than 2 microns or larger. In such an arrangement most, or all, of the additive is available for surface action, and, with wear and/or washings a small amount of the surface of the sheath will wear or wash away, and other additive particles which were originally more deeply embedded, become available at the surface.

Figure 5:
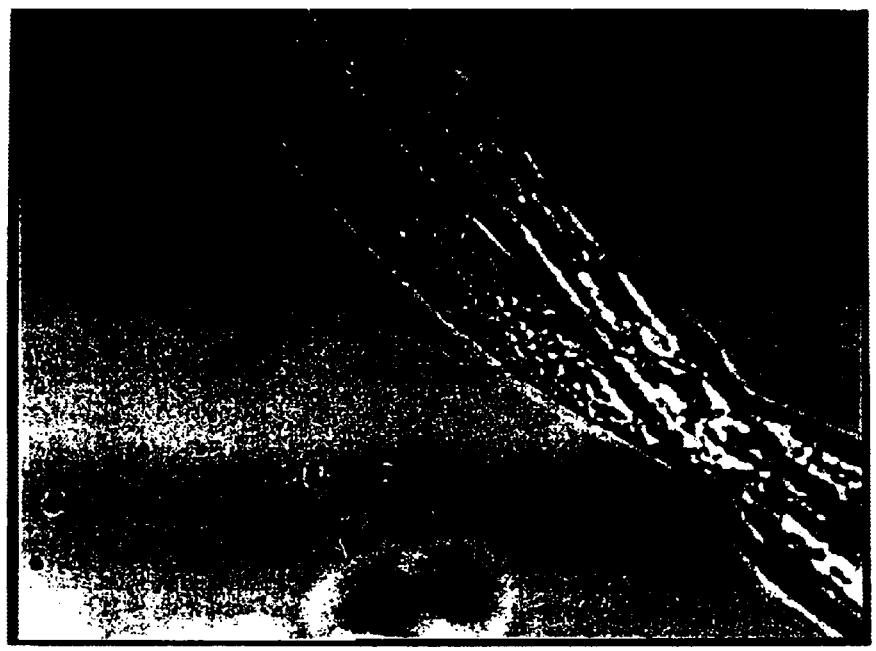
FIGS. 5 and 6 are photomicrographs of fibers showing the particles of zeolite of silver.
Figure 6:
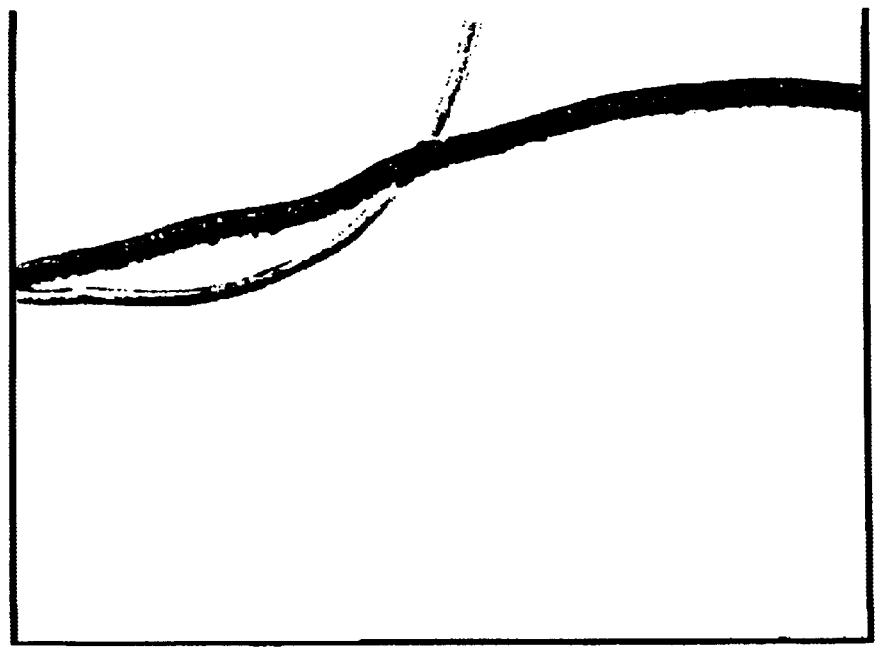

The photomicrographs of FIGS. 5 and 6 show the small particles of zeolite of silver in the sheath, many of which can be seen on the surface or projecting through to the surface of the fibers. There are more such particles which are just below the surface of the fibers, and which will become available for anti-microbial activity as small portions of the fiber wears or washes away and the particles become available at the surface.

Figure 3:
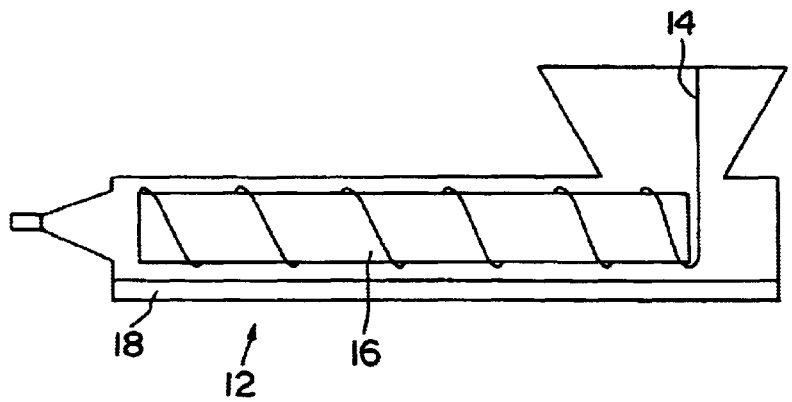
FIG. 3 is a schematic view of the feed hopper, screw and extruder.

FIGS. 3 and 4 show a manner of making a core/sheath fiber with an anti-microbial additive which is incorporated into the sheath polymer prior to the final extruding of the fiber. In the prior art, this was mostly done as a treatment after extruding.

The extruder 12 is shown diagrammatically in FIG. 3 having a feed hopper 14, an extruder screw section 16 for feeding melted material to the delivery end, and a heating chamber 18 which surrounds the bottom of the feed hopper as well as the total length of the extruder screw section 16 for melting the pellets which are fed into the hopper and maintaining the polymers in melted condition for being extruding through the extruding openings which act as nozzles. Besides pellets, it is possible to make these fibers using direct polymer streams from continuous reactors feeding to the melt pumps for a company which is a polymer producer.

There are two extruders, one which has a feed hopper for forming the sheath and another with a hopper for forming the core.

The nozzle end of the extruder is shown in cross section in FIG. 4 which includes three sheets of metal 20, 22 and 24 to form two chambers 26 and 28. The melted polymer is fed into the extruder nozzle from the top. There are a plurality of two types of holes, one type being 30 and which feeds into chamber 26 to form the core of the fiber, and the other type being 32 which feeds into chamber 28 to form the sheath of the fiber.

The following non-limiting examples illustrate practice of the invention.

EXAMPLES

Example 1

The anti-microbial fiber of the present invention was used in the making of a mattress pad. In this example, 15% of a 6.7 denier 76 mm cut length natural white fiber was used as a homofilament with zeolite of silver as the anti-microbial agent and 15% of a bi-component fiber was used together with 70% PET 6×3 T295 in a blend in which the zeolite of silver comprised 0.9% of the fiber. The blend of this fiber was made into a batt of about 1–1½" thickness of nonwoven material which was then placed between two layers of woven fabric to form a mattress pad. When tested using the shake flask test this provided a 99.99% microbial kill ratio.

There are other examples in which all of the parameters of Example 1 were used and in each of which there was 15% of a bi-component fiber used. Again the zeolite of silver comprised 0.9% of the fiber. The percentage of the anti-microbial fiber ranged from 20% to 40% and the PET ranged from 45% to 65%. In all examples the microbial kill ratio was 99.99% using the shake flask test.

Example 1A

In this example, 35% of a 6.7 denier 51 mm cut length natural white fiber was used in a sheath/core bi-component configuration with zeolite of silver as the anti-microbial agent and 15% of another bi-component fiber was used together with 50% PET 6×3 T295 in a blend in which the zeolite of silver comprised 1.8% of the fiber. The blend was then prepared as in example 1 and when tested using the shake flask test, there was a 99.9% microbial kill ratio.

A second group similar to the first one was prepared in which the sheath/core bi-component fiber with zeolite of silver as the anti-microbial agent comprised from 10 to 35% of the fiber blend, 15% of another bi-component fiber was used and from 50 to 75% of PET 6×3 T295 was used. The zeolite of silver comprised 0.75% of the fiber. In the shake flask test, there was a 99.99% microbial kill ratio.

Example 2

In this example, 15% of a 3.5 denier 38 mm cut length PETG fiber was used as a homofilament with zeolite of silver as the anti-microbial agent. 85% PET fiber was blended with the PETG anti-microbial fiber to form a blend in which the zeolite of silver comprised 1.8% of the fiber. The fiber was made into a wall covering and was tested by the shake flask test, which provided a microbial kill rate of 99.99%

A modified version was prepared the same way except that there was only 10% fiber with zeolite of silver in the blend and 90% PET fiber was used. After the fiber was made into a wall covering, this too provided a 99.99% microbial kill rate using the shake flask method of testing.

A further modified version was used in which there was only 5% fiber having zeolite of silver in the blend and 95% PET fiber in the blend. The testing, after the fiber was used in a wall covering, again provided a 99.99% microbial kill rate for bacteria.

The fibers described above can be used to make both woven and nonwoven fabrics as well as knitted fabrics. Such fabrics are useful for various types of articles, some of which are listed below:

INCONTINENT GARMENTS

Incontinent garments, including disposable diapers, underwear, pajamas, and linens, some of which may be knitted. This is disclosed, for example, in pending provisional application Serial No. 60/173,207 filed Dec. 27, 1999, the contents of which are physically incorporated herein below, in which garments and other articles for incontinent persons made of an anti-microbial fiber comprises various thermoplastic polymers and additives in a mono-component or bi-component form in either a core-sheath or side-by-side configurations. The anti-microbial synthetic fibers can comprise inorganic anti-microbial additives, distributed only in certain areas in order to reduce the amount of the anti-microbial agents being used, and therefore the cost of such fibers. The anti-microbial additives used in the synthetic fibers do not wash off over time because they are integrally incorporated into these fibers, thus their effectiveness is increased and prolonged. The anti-microbial synthetic fibers comprise high tenacity polymers (e.g. PET) in one component and hydrolysis resistance polymers (e.g. PCT) in another component. The hydrophilic and anti-microbial additives provide a hydrolysis-resistant surface with good wrinkle resistance that results in long-term protection against washings in boiling water and strong soaps. The anti-microbial synthetic fibers can further be blended with non-anti-microbial fibers such as cotton, wool, polyester, acrylic, nylon etc. to provide anti-microbial finished fabrics that are able to withstand significant wear and washings and while maintaining their effectiveness;Anti-microbial fibers can be used to make materials for a variety of applications in which it is necessary or desirable to reduce bacterial and fungal growth and the resultant odor. Specifically, in personal hygiene situations, these materials can be used in reusable or re-wearable incontinent garments and other articles such as linens and bed packs to prevent bed sores on persons confined to bed for extended periods of time. Diapers and other clothing and articles for incontinent individuals are constantly and intermittently being soaked with urine and these items as now manufactured are not effective at killing odor and infection-causing bacteria. By making these items disposable, the growth of bacteria and fungi is reduced depending upon how often they are changed, but there are environmental and other considerations to disposables. However, the use of the anti-microbial fibers in such garments and articles that maintain their effectiveness during washings, results in reusable garments and articles of the type described with odor reducing and anti-microbial properties which last for the life of such garments and articles.

As a result of the above, the use of anti-microbial fibers in the manufacture of incontinent garments is desirable.

These anti-microbial fiber-containing garments are useful in reducing the growth of bacteria, fungi, and other microbes once soaked with urine, thus reducing the discomfort of the individual and preventing infections generally. Specifically, the anti-microbial fiber-containing fabrics may be used in both the covering fabric and the water absorbent interior material. In this way, both surface and interior protection is achieved. In addition, these materials may also be made to be reusable because the anti-microbial effect of the fibers of these garments and articles are resistant to multiple washings. Thus, a significant cost savings is realized in the laundry operations of hospitals and nursing homes as well as in the economics of individual households.

In manufacturing these materials, any of the fiber embodiments described below could be used. Both the strength and resiliency of these materials is important since they must stand up to multiple wettings and subsequent cleanings. Thus, both bi-component fibers and mixed fiber fabrics are useful embodiments for incontinent garments. Also, other modifications of the characteristics of these fibers and fabrics beyond that of adding anti-microbial agents, including the addition of agents to increase or decrease hydrophobicity, are useful in view of the repeated wettings and the need for frequent cleanings and washings. In addition, anti-odor additives may be particularly useful in this application in light of this frequency of cleaning, as well as the wetting with urine. Thus, these anti-microbial materials, garments and articles significantly reduce the growth of mold, mildew, and bacteria in home and institutional environments.

Garments for incontinent persons are made of anti-microbial fibers designed to use inorganic silver-containing compounds that are integrated into the polymers that are used to make these anti-microbial fibers. However, other metals (such as copper, potassium, magnesium, and calcium) can be used as anti-microbial agents. In addition, mixtures of different metal-containing anti-microbial agents in differing concentrations can be used that result in hybrid agents tailored for specific tasks.

Such garments may be knitted or woven and include underwear, pajamas, linens, disposable diapers, and the like.

Figure 7:
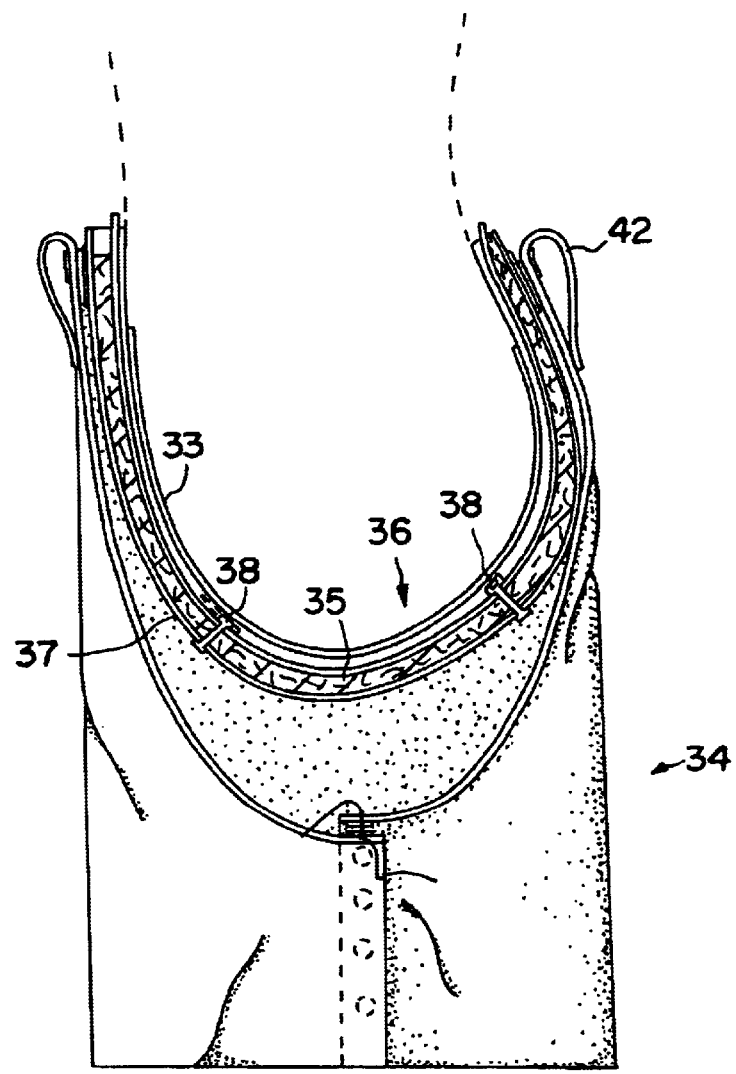
FIG. 7 shows a garment made from the fibers of the present invention for a person who is incontinent.

One type of such garment of the present invention is shown in FIG. 7 in which there is a garment 34 which carries a removable liner assembly 36 which is detachably secured within the garment. The liner assembly includes an outer layer 33 which contacts the skin of a wearer 44 around the buttocks and crotch area. This layer is made to be smooth and soft so as to be comfortable for the wearer even when fluids such as urine contact this layer and pass therethrough. There is a wick layer 35 which changes color when it is wet so that attendants can see from a distance that a wearer is wet and needs to receive some attention, such as the changing of the liner assembly. Beyond the layer 35 is an absorbent layer 31 formed of a mass of fibers. There is an inner layer 37 which is impervious to fluids so that the fluids such as urine do not wet and/or stain the outer layer of clothing. The liner assembly 36 is held together by soft fiber connectors 38. The liner itself may be removably attached to the basic garment with Velcro so that it is easily removable and changed.

The liners 36 may be constructed to be washable so that they can be reused, or can be made to be disposable. The garment has a belt 42 for holding the garment in place.

The outer layer 33 is made of anti-microbial fiber of the type described in further detail below so that there is protection from microbes and fungus which causes infection and odors.

Layer 33 is made to be a porous fiber material which will draw any moisture from the wearer by wick action away from the wearer's skin and into the absorbent liner. Since the layer 33 is always against the wearer's skin and at least at times is wet from urine, there is the risk of infection which, with the present invention is prevented, due to the layer 33 being constructed of anti-microbial fibers, the construction of which is described in more detail above.

The absorbent material 31 of the liner 36 may also be made of non-woven fibrous material which is also anti-microbial if desired.

Anti-microbial fibers may be made into other products intended for incontinent persons, such as bed linens, and bed packs which are used to prevent bed sores in persons who are confined to bed for extended periods of time. Such products provide a first line of attack against problems caused by microbes especially when used in all areas of the products which come into contact with a person's skin.

Higher loading of the anti-microbial agents (up to 5 times) is used to more effectively act against fungi. This higher loading may be achieved by using various zeolites followed by heating the fiber polymer, e.g. PET, to between 180 and 230 degrees Fahrenheit in hot water which allows further metal loading or ion exchange to replace resident metal ions with another ion or mixture of ions. In addition, this would allow the zeolite at or near the surface of the fiber to be preferentially loaded with the metal ion or mixtures thereof that has the desired biological effect. These methods are particularly useful in reducing costs when expensive metal ions, such as silver, are used in these processes. Also, by adding certain metals, e.g. silver, at this point in the process and not having it present during the high temperature fiber extrusion process, any yellowing or discoloration due to oxidation of the metal ion or its exposure to sulfur and halogens would be greatly reduced.

AIR FILTERS

Air filters for HVAC systems, air conditioning systems, car and airplane cabin systems as disclosed, for example, in Ser. No. 60/172,285 filed Dec. 17, 1999, the contents of which are physically incorporated herein below, in which filters and filter materials are made of anti-microbial fibers for a variety of filter applications in which it is necessary or desirable to reduce bacterial and fungal growth and their resultant odor. Specifically, in vehicles, such as automobiles, the air filters and attached air conditioning units are the source of musty smells associated with the seeding and growth of bacteria, fungi, mold, and mildew. Because of the recirculation of outside and air-conditioned air through these filters, very favorable conditions exist for the growth of bacteria, fungi, and other microbes. Also in aircraft cabins, the air filters have the same beneficial results. An anti-microbial filter is made of fiber, which comprises various thermoplastic polymers and additives in a mono-component or bi-component form in either a core-sheath or side-by-side configurations. The anti-microbial synthetic fibers can comprise inorganic anti-microbial additives, distributed only in certain areas in order to reduce the amount of the anti-microbial agents being used, and therefore the cost of such fibers. The anti-microbial additives used in the synthetic fibers do not wash off over time because they are integrally incorporated into these fibers, thus their effectiveness is increased and prolonged. The anti-microbial synthetic fibers comprise high tenacity polymers (e.g. PET) in one component and hydrolysis resistance polymers (e.g. PCT) in another component. The hydrophilic and anti-microbial additives provide a hydrolysis-resistant surface. The anti-microbial synthetic fibers can further be blended with non-anti-microbial fibers such as cotton, wool, polyester, acrylic, nylon etc. to provide anti-microbial finished filters that are able to withstand significant wear and washings and while maintaining their effectiveness. The foregoing objects concerning filters are met by filters based on anti-microbial fibers that have been designed using inorganic silver-containing compounds that allow the formation of both mono- and multi-component polymeric fibers having these anti-microbial agents intermixed within the polymer during fiber formation. The concentration of the anti-microbial agent can be varied within each individual fiber as a gradient using mixing strategies and also from fiber to fiber. The concentration of anti-microbial agent within a fabric or material made from these anti-microbial fibers can also be varied regionally using fibers containing varying amounts of anti-microbial agents in conjunction with both natural and synthetic fibers having different amounts of anti-microbial agents or even no added anti-microbial agents. A variety of other agents can be added, either by mixing or topically, to color the fibers and/or to make it resistant to staining, fire, and ultraviolet (UV) light as well as altering its water absorbing qualities. Various polymers, without limitation, can be used to form these fibers. In the context of this invention, anti-microbial refers, but is not limited, to anti-bacterial and anti-fungal.;

The amount of time people spend in their vehicles has been increasing over the last 20 years. The passenger compartment of these vehicles is an extension of people's personal space. The desired quality of the air in that space increasingly reflects peoples' desire to be protected from airborne particles and odors, and bacteria. Such vehicles include pick-up trucks, SUVs, recreational vehicles, buses, over-the-road trucks, and the like.

Anti-microbial fibers can be used to make filter materials for a variety of applications in which it is necessary or desirable to reduce bacterial and fungal growth and their resultant odor.

Specifically, the built in or attached air conditioning units for over the road vehicles are a source of musty smells associated with the seeding and growth of bacteria, fungi, mold, and mildew on the evaporator and or heater cores and housings. These areas, by their nature, collect dust, dirt, bacteria, mold spores, etc. in an environment that contains the moisture, temperature, and shielding from direct sunlight necessary to promote growth of these organisms.

A filter containing permanent anti-microbial fibers, described herein, could be placed in the outside make-up air and/or recirculated air streams to kill the spores and cells trapped by the filter. This would reduce or eliminate the odors associated with growing and reproducing organism.

The permanent nature of the anti-microbial fibers in the filter is necessary based on the environment of operation and desired replacement life. The filters are subjected to moisture from entrained water from the blower fan inlet (rain, or wash water) as well as condensation of moisture when the air conditioning system is in operation. Further, the vehicle owners, and vehicle design engineers, want a filter that has at least a one year life. Both conditions can be overcome with permanently anti-microbial fibers described herein.

Such anti-microbial fiber-containing filters are useful in reducing the build-up of biological materials and films on the filters themselves and the associated air conditioning units. Thus, they would also be less likely to impart undesirable odors to the interior of the vehicles.

In manufacturing these materials, any of the embodiments described above could be used. Both the strength and resiliency of these materials is important given that they are used in continuously circulating air streams and are subject to the pressures characteristic of filtering processes. Any number of filter shape designs could be used as appropriate. In some instances, round filters would be appropriate whereas in other instances pleated or other shape filters would be appropriate, all depending on the pressure, volume characteristics of the air flow and available space. Thus, both bi-component fibers and mixed fiber fabrics are useful embodiments for vehicle and aircraft cabin air filters. Also, other modifications of the characteristics of these fibers and fabrics beyond that of adding anti-microbial agents, including the addition of agents to increase or decrease hydrophobicity, would be useful. In addition, anti-odor additives may be particularly useful in this application given the use in connection with air conditioners.

Thus, these anti-microbial materials that are manufactured to be used in vehicle and aircraft cabin air filters will then significantly reduce the growth of mold, mildew, and bacteria. By achieving this goal, odors associated with the long-term use of these filter materials will be reduced. This will also then result in a significant costs savings in the operation of air recirculation systems in automobiles.

Figure 8:
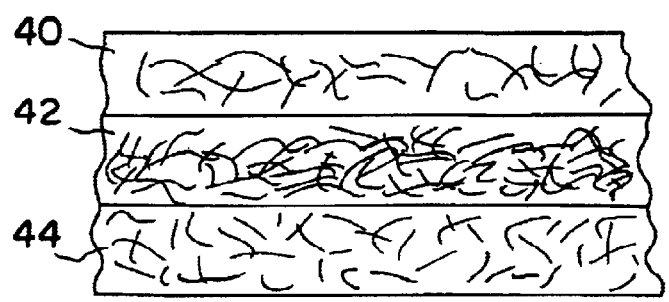
FIG. 8 is a cross section of one type of filter using the fibers of the present invention.

Filters for vehicle and aircraft cabins are, according to the invention, made of anti-microbial fibers which use inorganic silver-containing compounds that are integrated into the polymers that are used to make these anti-microbial fibers. Such a filter is shown diagrammatically in FIG. 8. The example shown in a typical progressive filter which has three layers. There is a support layer 44, then a filtration layer 42 made with anti-microbial fibers and then a prefilter layer 40 also made with anti-microbial fibers.

The relatively small size of the silver-containing zeolite compounds (2 microns and less) that are used in the manufacturing of the fibers allow these anti-microbial agents to be incorporated into fibers instead of being applied to them. For example, a bi-component fiber is made with the sheath having a thickness which is properly related to the cubic size of the zeolite particles. Zeolite particles have a one micron cube size would be placed into a sheath having a two micron thickness. Thus, because these anti-microbial agents are an integral part of the fiber, they are not washed or easily abraded away and the finished articles, in the present case, filters, manufactured from them are able to withstand significant wear and multiple washings while maintaining their anti-microbial effectiveness (for those filters which are washed). In the case of filters which are thrown away when they start to become clogged with filtered material (air borne particles and the like) the resistance to washings is not an important factor.

Figure 9A:
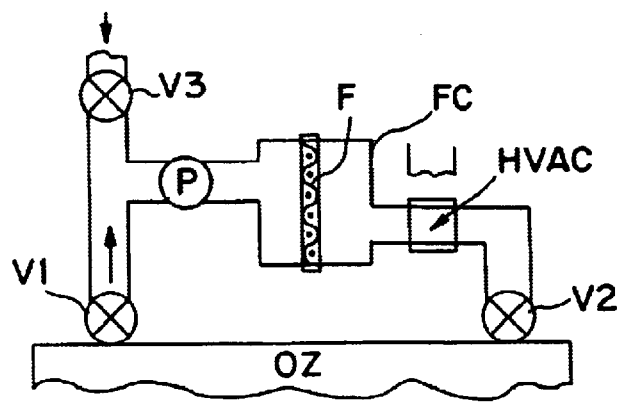
FIGS. 9A, 9B, 9C, 9D are diagrams of air flow systems utilizing the fibers of the invention.

FIG. 9A shows a system of filter usage for an occupancy zone where air is removed via valve V1 through a pump or compressor P passed through a filter canister F (or other container) and a heating or cooling exchanger (HVAC) and returned to the occupancy zone via valve V2. The system can also handle outside air via a valve V3.

The canister has a removable anti-microbial filter screen F (with a frame, not shown) removable for exchange or regeneration of anti-microbial effectiveness from time to time.

Figure 9B:
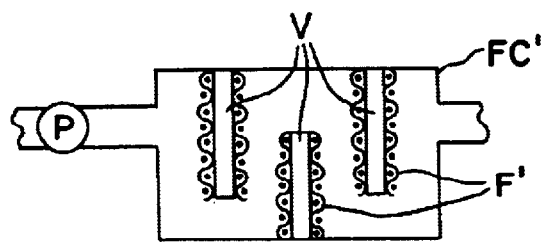

Another form of filter is shown in FIG. 9B as filter canister FC' with vanes V defining a tortuous path, the vanes being lined with anti-microbial screening material F'.

Figure 9C:
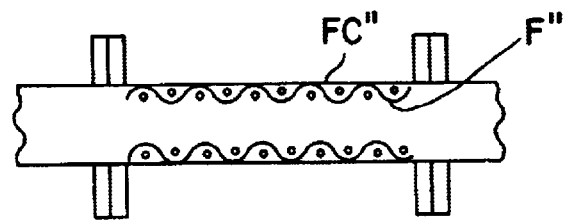
Figure 9D:
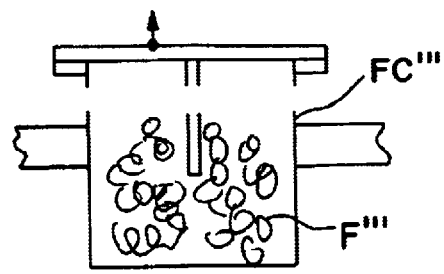

FIG. 9C shows another form of canister as a tube FC" lined with such filter material F" and FIG. 9D shows a canister FC''' with a loose array of filter material F''' (similar to a scouring pad).

WOUND CARE DRESSINGS AND BURN DRESSINGS

Wound care dressings and burn dressings made of fibers as disclosed, for example, in Ser. No. 60/172,533 filed Dec. 17, 1999, the contents of which are physically incorporated herein below in which an anti-microbial wound care dressing or burn dressing is made of fiber such as various thermoplastic polymers and additives in a mono-component or bi-component form in either a core-sheath or side-by-side configurations. The anti-microbial synthetic fibers can comprise inorganic anti-microbial additives, distributed only in certain areas in order to reduce the amount of the anti-microbial agents being used, and therefore the cost of such fibers. The anti-microbial additives used in the synthetic fibers do not wash off over time because they are integrally incorporated into these fibers, thus their effectiveness is increased and prolonged. The anti-microbial synthetic fibers comprise high tenacity polymers (e.g. PET) in one component and a hydrolysis resistance polymer, PCT, in another component. The hydrophilic and anti-microbial additives provide a hydrolysis-resistant surface with good abrasion resistance. The anti-microbial synthetic fibers can further be blended with non-anti-microbial fibers such as cotton, wool, polyester, acrylic, nylon etc. to provide anti-microbial finished wound care dressings and burn dressings that are able to withstand significant wear and any washings they may be given (if the washable type) and while maintaining their effectiveness.

Wound care dressings may be made with anti-microbial fibers used to make various materials for a variety of applications in which it is necessary or desirable to reduce bacterial and fungal growth. Because these dressings must be frequently changed and the wound exposed to pathogens during this changing process, the addition of anti-microbial agents to the wound care dressing helps to reduce the growth of these pathogens.

As a result of the above, the use of anti-microbial fibers in the manufacture of wound care dressings provides a practical medical article. These anti-microbial fiber-containing dressings are useful in reducing the growth of bacteria, fungi, and other microbes that can be introduced from the environment during the changing of dressings and while performing other manipulations, thus reducing and preventing infections generally. Specifically, the anti-microbial-fiber containing fabrics could be used in both the covering fabric and the water absorbent interior material. In this way, both surface and interior protection could be achieved. In addition, these materials could, if desired, be made to be reusable because the anti-microbial effect of the fibers of this invention are resistant to multiple washings. Thus, a significant cost savings could be realized in the purchasing of supplies in hospitals and nursing homes as well as in the economics of individual households.

In manufacturing these materials, any of the embodiments of fibers described above could be used. Both the strength and resiliency of these materials is important in that they must withstand normal patient movement and manipulation by health care workers. Thus, both bi-component fibers and mixed fiber fabrics are useful embodiments for wound care dressings. Also, other modifications of the characteristics of these fibers and fabrics beyond that of adding anti-microbial agents, including the addition of agents to increase or decrease hydrophobicity, would be useful in manufacturing sturdy dressings. In addition, anti-odor additives may be useful in this application given the exposure of the dressing to various tissue exudates. Thus, these anti-microbial materials would then significantly reduce the growth of mold, mildew, and bacteria in wound care dressings.

Burn dressings may be made with anti-microbial fibers to make various materials for a variety of applications in which it is necessary or desirable to reduce bacterial and fungal growth. Because these dressings must be frequently changed and the burn exposed to pathogens during this changing process, the addition of anti-microbial agents to the burn dressing would help to reduce the growth of these pathogens.

As a result of the above, the use of anti-microbial fibers in the manufacture of burn dressings is a desirable goal. These anti-microbial fiber-containing dressings are useful in reducing the growth of bacteria, fungi, and other microbes that can be introduced from the environment during the changing of dressings and while performing other manipulations, thus reducing and preventing infections generally. Specifically, the anti-microbial-fiber containing fabrics can be used in both the covering fabric and the water absorbent interior material. In this way, both surface and interior protection may be achieved. In addition, these materials can be made to be reusable because the anti-microbial effect of the fibers of this invention are resistant to multiple washings. Thus, a significant cost savings could be realized in the purchasing of supplies in hospitals and nursing homes as well as in the economics of individual households.

Figure 10:
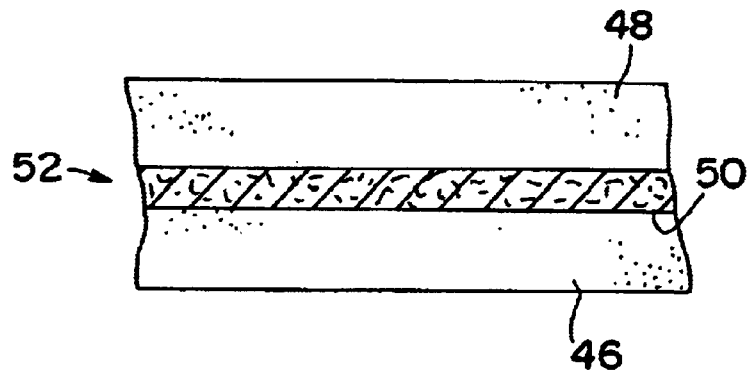
FIG. 10 is a cross section of one type of wound care or burn dressing.

FIG. 10 shows a wound care or burn dressing 24 which includes a bottom layer 18, a top layer 20 and an intermediate absorbent fibrous layer 22 which joins the other two layers. The bottom layer 18 is used directly against the wound or burn and therefore the fibers of this layer have the anti-microbial agent applied thereto as described below.

In manufacturing these materials, any of the embodiments of fiber described above can be used. Both the strength and resiliency of these materials is important given that they must withstand normal patient movement and manipulation by health care workers. Thus, both bi-component fibers and mixed fiber fabrics are useful embodiments of burn dressings. Also, other modifications of the characteristics of these fibers and fabrics beyond that of adding anti-microbial agents, including the addition of agents to increase or decrease hydrophobicity, would be useful in manufacturing sturdy dressings. In addition, anti-odor additives may be useful in this application given the exposure of the dressing to various tissue exudates. Thus, these anti-microbial materials would then significantly reduce the growth of mold, mildew, and bacteria in burn dressings.

Fiber and fabric which are color-fast and which can be for pastel shade fabric, as disclosed, for example, in Ser. No. 60/180,536 filed Feb. 7, 2000, the contents of which are physically incorporated herein below, in which PETG which is an amorphous binder fiber is used and is blended into yarns with other fibers to form fabrics, as well as knits and non-woven fabrics. After heat activation, the PETG fiber melts, wets the surface of the surrounding fibers, and settles at the crossing points of the fibers, thus forming "a drop of glue" which bonds the fibers together. PETG is also used to carry pigments and/or anti-microbial additives to the fibers, distribute the pigment and/or anti-microbial additives on the surface of the surrounding fibers, and achieve certain colors without the need to dye the fibers and natural fabrics having anti-microbial qualities. This invention presents a method for making a pastel shade fabric and/or nature fabrics having anti-microbial activities by using PETG as a carrier for pigments and anti-microbial additives, blending them with cotton or any other fibers, activating and melting PETG from 110° to 140° C., and leaving the encapsulated pigment and anti-microbial additives on the fibers. The final pastel shade fabric having an excellent fastness for both sunlight resistance and washing without the need of going through a dye bath, and has the color remain fast for in excess of 100 commercial launderings. If the pastel shade fabric is made by blending PETG and pigments with cotton, after the activation of PETG, the final product can still be labeled as 100% cotton fibers. Thus, the present invention provides a fiber, yarn and/or fabric construction. There is a method for making a fiber blend which includes mixing a polyester polymer, characterized by a low melting temperature and having binder qualities, with an additive for providing desired characteristics to a finished fiber. The mixture is heated and extruded to form a continuous filament. The continuous filament fiber is cut to form a cut filament fiber. The cut filament fiber is blended with a natural fiber to form a fiber blend. The fiber blend is heated to a temperature in the melting temperature range of said polyester polymer for a sufficient period of time to melt the low melting temperature polyester polymer and wet the natural fiber and provide such natural fiber with the additive firmly attached thereto. The polyester polymer may be PETG. After the fiber is prepared it may be spun to make a yarn and the yarn may be made into a fabric. The heating step can take place after the yarn is made into a fabric. The additive may be a colorant, an anti-microbial agent, a fire retarding agent, or another agent which adds properties to the fiber or yarn or fabric. There is another method for making a fiber, which includes mixing a polyester polymer, characterized by a low melting temperature and having binder qualities, with an additive for providing desired characteristics to a finished fiber, heating the mixture and extruding it to form a continuous filament. Another polymer is heated and extruded to form a continuous filament. The extruding steps form a bi-component fiber with the mixture forming the sheath and the other polymer forming the core. The sheath is heated to a temperature in the melting temperature range of the polyester polymer for a sufficient period of time to melt the low melting temperature polyester polymer and wet the core fiber and provide the core fiber with the additive firmly attached thereto. The fabric invention provides a unique way to use polymers such as PETG to carry and deliver pigments and/or anti-microbial or other additives to a natural fiber, such as cotton, wool, and the like, and generate a final pastel shade fabric without losing the natural fiber's characteristics and/or natural fabric having anti-microbial properties.

PETG is used as a carrier for pigments, such as carbon black, phthalo blue, and the like. It is mixed with other fibers, such as natural fibers, to form a blend, and then the blend is heated, to a temperature of around 140° C. (the PETG can be modified to melt between 90 and 160° C.) either as a separate heating step or during a processing step which includes heating to about temperature. PETG has a melting temperature of around 140° C. (and is available from 90 to 160° C.) and it melts and flows along the fibers with which it is blended. It acts as a binder-carrier in that it forms nodes of color (when a colorant is used) with many points so it looks like a solid color. This provides it with a pastel look. By controlling the amount of colorant added to the PETG there is controllable color values which include pastel shading. PETG has superior wetting ability and therefore it spreads evenly along the other fibers with which it is blended. There are also nodes formed at the intersecting fibers in the blend and there are held together by this characteristic of the PETG. Also, the amount of PETG can be controlled to be small quantities with respect to the other fibers in the blend. Thus, when blended with cotton in this manner, such a blend may properly be characterized as "all cotton" having color and/or anti-microbial (or other) agents, which have been added by the PETG.

Figure 11:
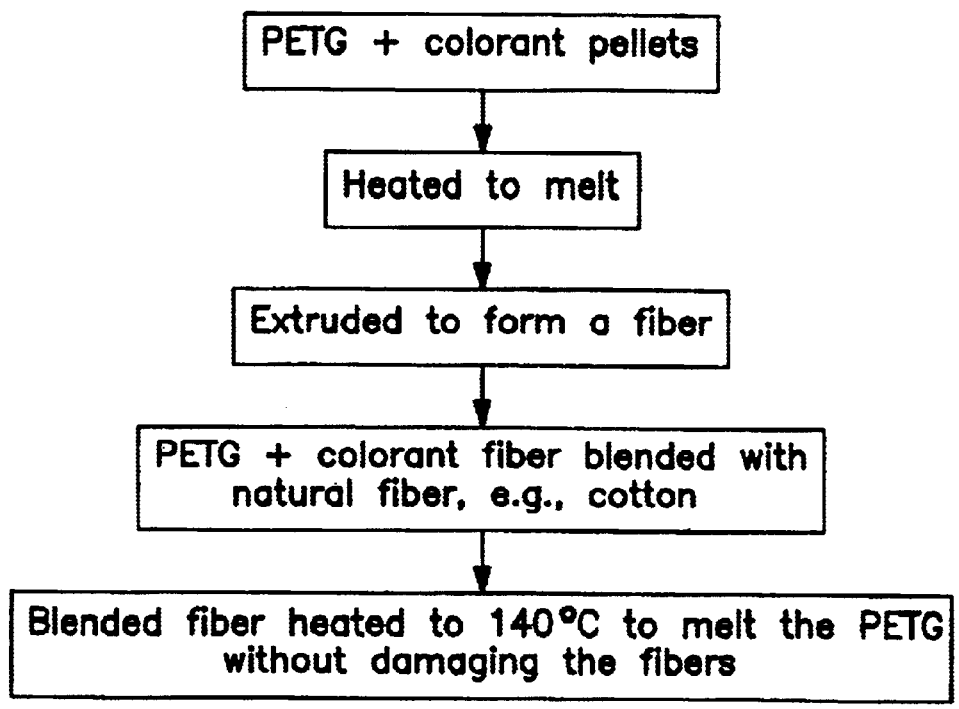
FIG. 11 is a flow chart showing the preparation of the fibers and yarn for use in making a woven or nonwoven fabric.

This can be accomplished in more than one manner. One method is shown in FIG. 11 in which the PETG and colorant pellets are mixed together, after which they are heated to melt and are then extruded to form a PETG fiber with the colorant in it. The PETG is then blended with a natural fiber, such as cotton, to form a blend, which will have the color of the colorant, which the PETG fiber takes on as its color. The cotton is white so that the color taken on is a pastel color. If the colorant is black, then the blend becomes a shade of gray. If desired other fibers can be blended with the PETG fibers, such as silk, flax, polypropylene, polyethylene, wool, polyester, acrylic, nylon, PTT, 3GT, rayon, modified rayon, and acetate.

The PETG is then activated by heating it as a temperature of from about 110° to about 140°. This melts the PETG without harming the fibers with which it has been blended. The PETG carrier melts and wicks along the other fibers, that is the cotton or other base fibers, forming small nodes, but it does not ball up as some polymers do and provides "a drop of glue" (small) to bind the fibers together and leaves behind the encapsulated pigment in the fibers.

This fiber blend is then used to form a yarn with in turn is used to form a fabric. The resulting fabric is a pastel shade fabric without the need of going through a dye bath, and has excellent color fastness from both sunlight and washing. The color is a pastel since there are many tiny drops of the colorant which looks like a solid color to an observer. The color remains fast for in excess of 100 commercial launderings. Since the PETG carrier melted after activation, the blended fibers such as cotton are still considered to be 100% cotton fiber.

Figure 12:
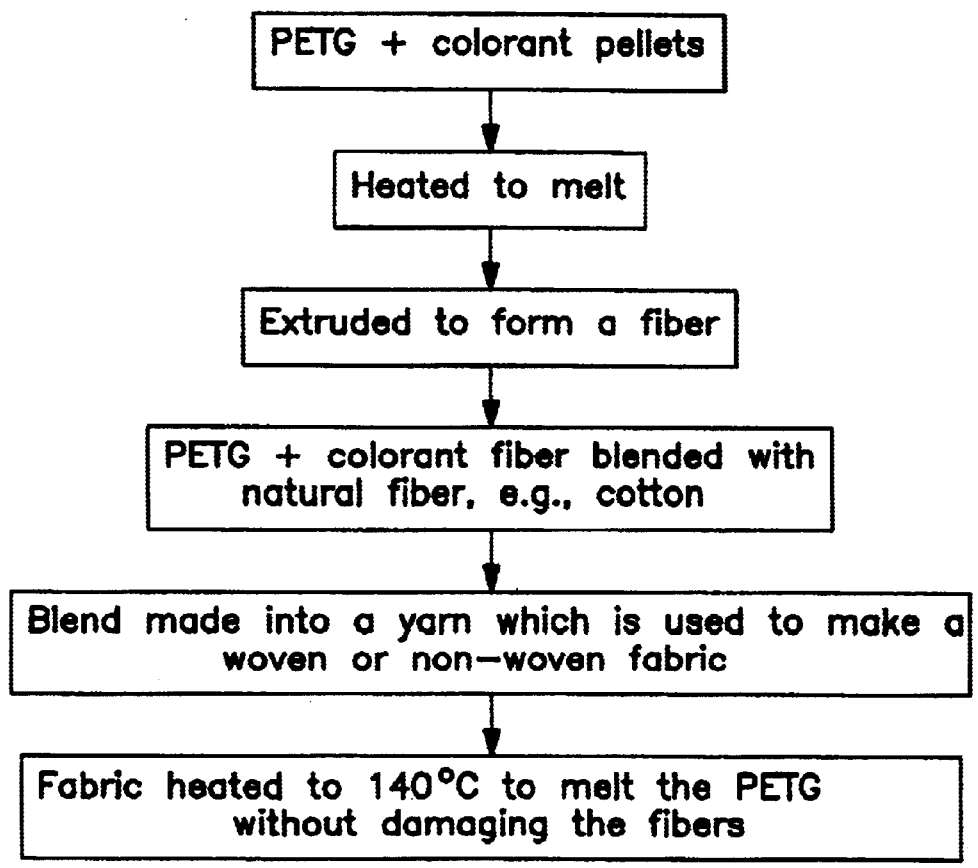
FIG. 12 is a flow chart showing the preparation of fibers and yarn and then of a fabric.

FIG. 12 shows a method similar to that shown in FIG. 11. However, in this process the blended fiber is made into a yarn and the yarn is made into a fabric before the PETG is activated by heating. This heating may be a separate heating step or may take place during the processing of the fabric which may include a heating step for other reasons.

The present invention may also be used to provide anti-microbial fibers by using PETG as a carrier for anti-microbial additives. Again the PETG and the anti-microbial pellets may be melted together to form a melt which is extruded to create a continuous filament which is then cut to appropriate size and is then further blended with natural or other fibers to provide an anti-microbial finished yarn which may be made into an anti-microbial fabric that is able to withstand significant wear and washings and maintain their effectiveness. The anti-microbial additives are inorganic compounds made from metals such as copper, tin, zinc, silver, and the like. The preferred compound is a zeolite of silver which may be dispersed in PE, PET, or PBT before being added to the fiber. The additives can be added directly to the primary polymer with pre-dispersion. The total active ingredients range from 0.1 to 20% by fiber weight. Other inorganic metals such as tin, copper and zinc work also, but not as well as zeolite of silver.

The PETG polymers with anti-microbial additives can be blended with natural fibers such as cotton, silk, flax, and wool, or synthetic fibers such as polyester, polypropylene, polyethylene, acrylic, nylon, PTT, 3GT, rayon, modified rayon, and acetate to make anti-microbial finished fabrics that are able to withstand significant wear and washings and maintain their effectiveness.

A typical example is a fiber using the PETG polymer with the zeolite contained silver additive blended with cotton up to 10% by weight to produce a bed sheet. The binder fiber is activated during the drying cycle of the final bleaching operation or other heat operation. The PETG melts and wets the surface of the cotton fibers to carry the anti-microbial characteristics to the entire sheet with an added benefit of increasing strength and reducing pilling.

The fiber size ranges from 0.7 dTex to 25 dTex and a staple length of 1.0 mm to 180 mm. A continuous filament yarn can also be produced that can be used in a wrap spun application whereby fibers are spun around the anti-microbial filament.

The anti-microbial product withstands more than 50 commercial washings at 80° C. It is immune to UV exposure of at least 225 kj. It possesses excellent abrasion resistance and is unaffected by tests such as Tabor or Wyzenbeek. It is not affected by at least 50 dry cleanings.

Figure 13:
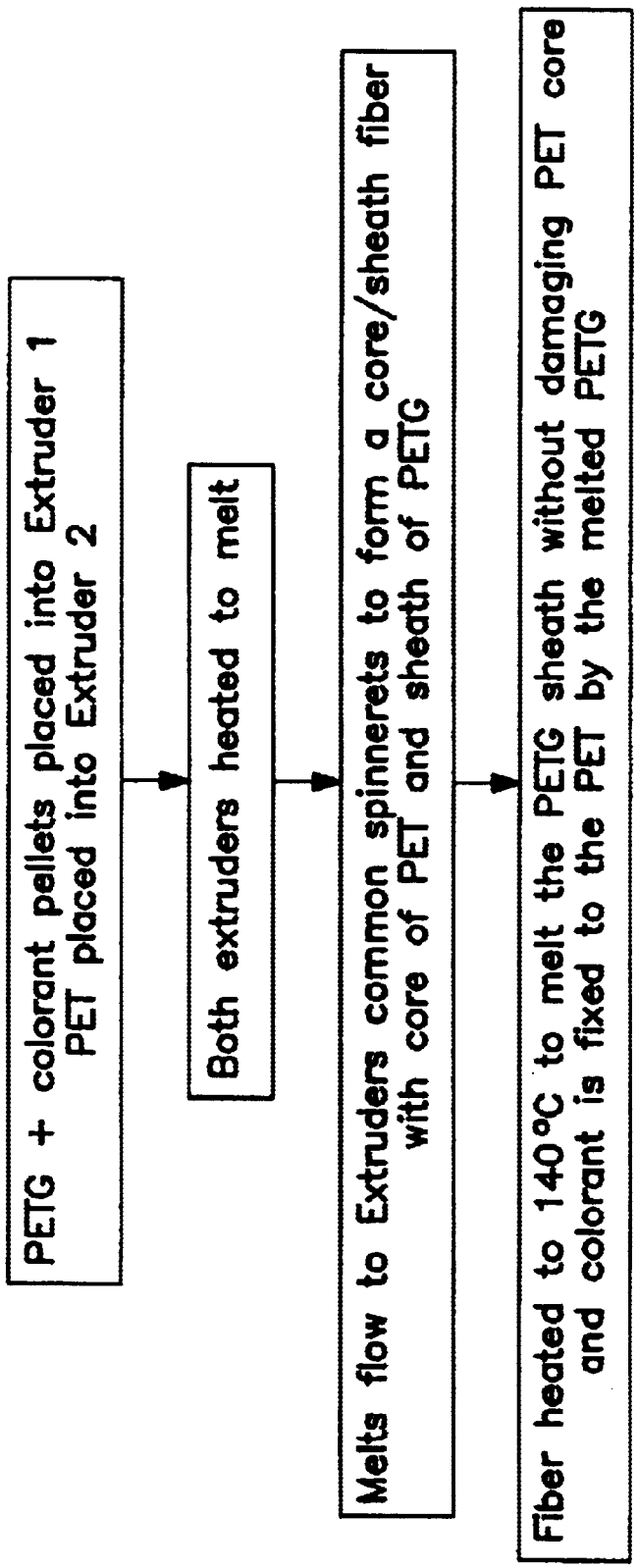
FIG. 13 is a flow chart showing another manner of preparing fibers in accordance with the present invention.

FIG. 13 is another flow diagram for an arrangement, which provides a bi-component fiber with a PET core and a PETG sheath containing a desired additive, such as pigment and/or an anti-microbial agent. The PETG and the colorant pellets are placed into a first extruder and PET pellets are placed into a second extruder. Both are heated sufficiently so that the extruders cause the melts to flow to a single spinneret in which the PET is made into the core and the PETG is made into the sheath. In the fiber state, or in a more finished yarn state, or in an even further finished woven or nonwoven fabric state, the fibers are subjected to heat in the vicinity of 140° C. which melts the PETG without harming the PET which has a higher melting point. This heating step provides the benefits of the present invention as discussed above.

Footwear components as disclosed, for example, in pending provisional application Serial No. 60/181,251 filed Feb. 9, 2000, the contents of which are physically incorporated herein below, in which the footwear components provide several embodiments of anti-microbial and/or anti-fungal footwear products. The footwear components such as insoles, midsoles, box toes, counter and linings of footwear products, e.g., shoes, slippers, sneakers and the like are provided in which the anti-microbial agent is available for the life of the product and not washed away or worn away by sweat or abrasion. Also, the anti-microbial agent is placed into the component close to or on the surface which is most needy of the protection, such as the part of an insole closest to the foot of a user when the insole, or other component is assembled into a footwear product. Thus, the fungi or microbes which may form and create odors or other problems are killed on contact with the surface of the shoe component anti-microbial surface area. The footwear components can be a nonwoven fabric of synthetic fibers, primarily polyester, but which could be acrylic, nylon, rayon, acetate, PP, and the like. The fabric can have a weight from 65–400 grams per square meter and typical fibers range from 1.2 dTex to 7 dTex with a cut length of 25–76 mm. They are carded, cross-lapped and needle punched, but could be produced on other types of nonwoven equipment, such as spun laced or spun bonded equipment. The impregnation is a latex of SBR, vinyl acetate, PVC, acrylonitrile, and the like. Impregnation is from 1–4 times the weight of the nonwoven fabric on a dry basis. A range of fillers such as clay, calcium carbonate, and the like are used to reduce the cost. There are two basic methods. One is to mix the anti-microbial with latex compound and impregnate it into the insole. The other is to use anti-microbial fibers on the insole in various manners; The footwear components are provided by several embodiments described herein but may be practiced using other embodiments. There is described below, a first embodiment of a single layer of latex, and a second embodiment of a main support layer and a fiber layer attached thereto.

The foregoing objects are met by footwear components such as insoles, midsoles, box toes, counter and linings of footwear products, e.g., shoes, slippers and sneakers in which the anti-microbial agent is available for the life of the product and not washed away or worn away by sweat or abrasion. Also, the anti-microbial agent is placed into the component close to or on the surface which is most needy of the protection, such as the part of an insole closest to the foot of a user when the insole, or other component is assembled into a footwear product. Thus, the fungi or microbes which may form and create odors or other problems are killed on contact with the surface of the shoe component anti-microbial surface area.

The footwear component can be a nonwoven fabric of synthetic fibers, primarily polyester, but which could be acrylic, nylon, rayon, acetate, PP, and the like. The fabric can have a weight from 65–400 grams per square meter and typical fibers range from 1.2 dTex to 17 dTEx with a cut length of 15–180 mm. They are carded, cross-lapped and needle punched, but could be produced on other types of nonwoven equipment, such as spun laced or spun bonded equipment.

The impregnation is a latex of SBR, vinyl acetate, PVC, acrylonitrile, and the like. Impregnation is from 1–4 times the weight of the nonwoven fabric on a dry basis. A range of fillers such as clay, calcium carbonate, and the like are used to reduce the cost. There are two basic methods. One is to mix the anti-microbial with latex compound and impregnate it into the insole. The other is to use anti-microbial fibers on the insole in various manners.

Figure 14:
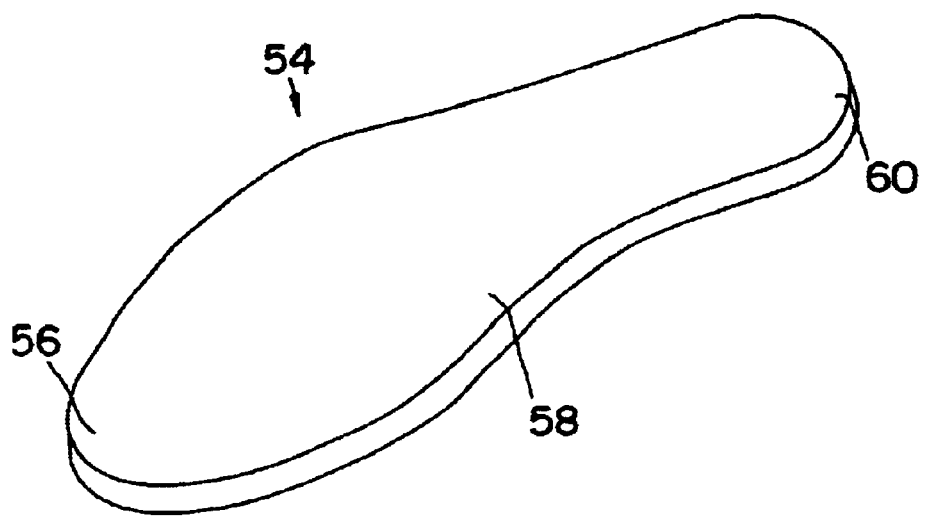
FIG. 14 is a schematic isometric view of a first type of insole using latex.

An embodiment of a nonwoven fabric impregnated with latex is shown in FIG. 14 in which there is an insole 54 having a toe portion 56 and a mid sole portion 58 and a heel portion 60 all in a single piece construction. It is a suitable fabric which is then impregnated with latex to provide cushioning for wearer comfort. The anti-microbial, in this case zeolite of silver is mixed with the latex prior to impregnating the insole.

Figure 15:
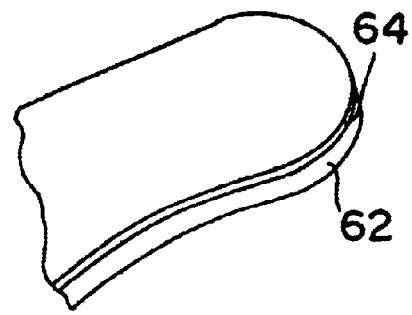
FIG. 15 is a schematic isometric view of a second type of insole using a layer of anti-microbial fibers.

FIG. 15 is another arrangement wherein a support and cushioning layer 62 is provided and which may be any of a number of materials which are used for insoles, but preferably one which of a nonwoven material. A fiber layer 64 made of fibers which have the anti-microbial agent disposed therein is attached to cushioning and support layer 62 by any suitable means. In this arrangement zeolite of silver is the anti-microbial agent. This can include an adhesive, but could also be accomplished by making the support layer of a polymer which is also used for some of the fibers and the fiber layer 64 is attached to the support layer 62 as the support layer is first delivered after being prepared and still retains the heat of preparation whereby the common polymer is hot enough to partially melt and then become bonded together.

Some anti-microbial agents are also anti-fungal agents. When agents do not perform both functions, a second agent will usually be used.

The choice of particle size of the zeolite is based on the thickness of the layer carrying it to obtain the best combination of surface area with anchoring in the layer. For example, a very thin layer of 3µ would be best served with a 1–2µ zeolite, which would have a maximum dimension of 2×1.73 or about 3.5µ.

The inner layer(s) could be made of basically any thermoplastic resin, such as; PE, PP, PET, PS, PCT, Polyamide (nylon), Acrylic, PVC, etc. The surface layer(s) could be made of the same polymers plus some low temperature ones such as PETG, Polycaprolactone, EVA, etc.

It is preferable to have the layer closest to a wearer's foot have the anti-microbial and/or anti-fungal agent and be porous to perspiration to absorb perspiration.

In the event a support layer is used which is not fibrous, it is covered with a nonwoven fabric, the fibers of which have the anti-microbial agent therein. Such a layer can be thinner than the support layer. However, it is usually best if the layers used allow perspiration to be carried away from the wearer's foot for both comfort and health reasons.

The anti-microbial particles are bonded into the surface layer and remain there for the life of the material and provide anti-microbial properties for the entire time.

It is advantageous to have the anti-microbial agent only at the surface since this is the only area which comes into contact with microbes and fungi, and to have the agent located in other places is wasteful.

Anti-microbial fibers can be used to make the footwear products of the present invention where it is necessary or desirable to reduce bacterial and fungal growth and their resultant odor. In manufacturing these materials, any of the embodiments of fiber described can be used. Both the strength and resiliency of these materials is important. Any number of shaped designs could be used as appropriate.

Also, other modifications of the characteristics of these fibers and material beyond that of adding anti-microbial agents, including the addition of agents to increase or decrease hydrophobicity, would be useful. In addition, anti-odor additives may be particularly useful.

The relatively small size of the silver-containing zeolite compounds (2 microns and less) that are used in the manufacturing of the fibers allow these anti-microbial agents to be incorporated into fibers instead of being applied to them. Thus, because these anti-microbial agents are an integral part of the fiber, they are not washed away by perspiration or easily abraded away and the finished components, such as insoles, manufactured from them are able to withstand significant wear while maintaining their anti-microbial effectiveness.

Specifically, higher loading of the anti-microbial agents (up to 5 times) is used to more effectively act against fungi. This higher loading may be achieved by using various zeolites followed by heating the fiber polymer, e.g. PET, to between 180 and 230 degrees Fahrenheit in hot water which allows further metal loading or ion exchange to replace resident metal ions with another ion or mixture of ions. In addition, this would allow the zeolite at or near the surface of the fiber to be preferentially loaded with the metal ion or mixtures thereof that has the desired biological effect. These methods are particularly useful in reducing costs when expensive metal ions, such as silver, are used in these processes. Also, by adding certain metals, e.g. silver, at this point in the process and not having it present during the high temperature fiber extrusion process, any yellowing or discoloration due to oxidation of the metal ion or its exposure to sulfur and halogens would be greatly reduced.

It is also possible to use these integrated anti-microbial compounds to make shoe components and products that have a varying distribution of the anti-microbial agent. For example, by varying the concentrations of the anti-microbial agent during mixture with the fiber-forming polymers, fibers having varying anti-microbial content can be formed which can then be added in varying amounts to form materials having varying concentrations of anti-microbial agents. In addition, the amount of anti-microbial present in the fiber itself can be varied, either lengthwise or in cross-section. Similarly, higher and lower concentrations of these anti-microbial agents in the overall fibers can be achieved by using multi-layered sheets in which, for example, the anti-microbial agent is present only in an outer layer section, thus significantly reducing manufacturing and selling costs. Any of the above manufactured anti-microbial fibers can be mixed with fibers that do not contain anti-microbial agents such that products can be made having overall and localized variations in concentrations of anti-microbial agents.

In addition, the fibers can be made either hydrophilic or hydrophobic as desired by mixing other agents into the fiber polymers or applying them to the fiber surface. By modifying the wetability characteristics of the fibers, they can be made more useful for various applications. For example, hydrophilic fibers are effective in applications in which one wants the anti-microbial material to more easily absorb water, such as when the material is designed to be used in footwear. Alternatively, hydrophobic films or fibers are effective in applications in which one wants to avoid the absorption of such solutions. For example, the insole of the present invention could be made with a hydrophilic agent on the upper surface which will be nearer to the foot of the wearer, while the lower surface which will be adjacent other parts of the footwear, could be made with a hydrophobic to keep the perspiration away from other parts of the footwear.

SHEET MATERIAL

سheet material as disclosed, for example in pending provisional application Serial No. 60/180,240 filed Feb. 4, 2000, the contents of which are physically incorporated herein below, in which flat or shaped sheets or films, including wide sheets can be individually extruded or there can be co-extrusion of flat or shaped films or profiles. The product may be a multi-layer construction with the surface layer, on one or both sides, containing zeolite of silver (or other metal such as tin, copper, zinc, etc.). The product may be a flat film for use in a flat form for counter tops, floors, walls, or molded into shapes such as cafeteria trays, shoe insoles, serving dishes, high chair table, refrigerator trays, microwave liners, and luggage. As a profile the extrusion may be a rain gutter, a screen enclosure, a counter top, hand railing, duct work, sanitary piping, water pipe, gasket materials around dishwashers, and the like. The same concept applies to multi-layer injection molded parts. In this case the surface layer may have anti-microbial properties in applications such as telephone handsets, baby bottles, computer keyboards, plastic utensils, milk bottles, and the like. The choice of particle size of the zeolite is based on the thickness of the film to obtain the best combination of surface area with anchoring in the film. For example, a very thin film of 3 p would be best served with a 1–2µ zeolite, which would have a maximum dimension of 2×1.73 or about 3.5µ. The inner films could be made of basically any thermoplastic resin, such as; PE, PP, PET, PS, PCT, Polyamide (nylon), Acrylic, PVC, etc. The surface layer(s) could be made of the same polymers plus some low temperature ones such as PETG, Polycaprolactone, EVA, and the like. Anti-microbial films are used to make sheet materials for a variety of applications in which it is necessary or desirable to reduce bacterial and fungal growth and their resultant odor. An anti-microbial sheet material is made of film which comprises various thermoplastic polymers and additives. The anti-microbial synthetic films can comprise inorganic anti-microbial additives, distributed only in certain areas in order to reduce the amount of the anti-microbial agents being used, and therefore the cost of such films. The anti-microbial additives used in the synthetic film do not wash off over time because they are integrally incorporated into these films, thus their effectiveness is increased and prolonged. The anti-microbial synthetic films comprise high tenacity polymers (e.g. PET) in one component and hydrolysis resistance polymers (e.g. PCT) in another component. The hydrophilic and anti-microbial additives provide a hydrolysis-resistant surface. If desired, fibers may be included and extruded. For example, such fibers could be used to make the two outer layers of the sheet material using sheath/core arrangements so that the anti-microbial agent is only present in the sheath to reduce the amount of anti-microbial agent which is used;The present invention provides several embodiments, some of which relate to the co-extrusion of flat or shaped films, sheets or profiles. The product may be a co-extruded multi-layer construction with the surface layer, on one or both sides, containing an inorganic anti-microbial and/or anti-fungal agent.

The product may be a flat film for use in a flat form for such uses as counter tops, floors, walls, or molded into shapes such as cafeteria trays, serving materials around dishwashers and garage doors.

The same concept applies to multi-layer injection molded parts. In this case the surface layer may have anti-microbial properties in applications such as telephone handsets, baby bottles, computer keyboards, plastic utensils, milk bottles, automotive interior parts, aircraft/bus/train seat and trim parts, and the like.

When the anti-microbial is zeolite of silver, the choice of particle size of the zeolyte is based on the thickness of the film to obtain the best combination of surface area with anchoring in the film. For example, a very thin film of $3\mu$ would be best served with a $1-2\mu$ zeolite, which would have a maximum cubic dimension of $2\times1.73$ or about $3.5\mu$. In this manner the anti-microbial particles are at least partially exposed and are not completely embedded in the thermoplastic material where they would have no anti-microbial effect unless the covering surface were abraded away.

The inner films or layers can be made of basically any thermoplastic resin, such as; PE, PP, PET, PS, PCT, Polyamide (nylon), Acrylic, PVC, etc. The surface layer(s) can be made of the same polymers plus some low temperature ones such as PETG, Polycaprolactone, EVA, etc.

Sheet Material Laminates

Figure 16:
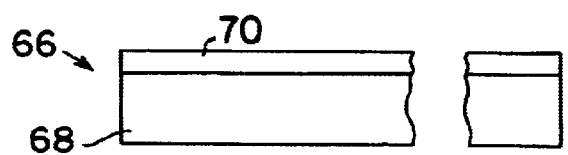
FIG. 16 is a side view of a sheet material having an anti-microbial film layer co-extruded thereon.

FIG. 16 shows one type of multi-layer sheet in accordance with the present invention. The multi-layer sheet material 66 has a main, thicker support layer 68 and a surface layer 70 which is a thin layer of a thermoplastic material which is sufficiently thin that small particles of anti-microbial agent are contained therein and have portions thereof which are at the surface or just below the surface of the layer. In this way the anti-microbial particles are bonded into the surface layer 70 and therefore remain there for the life of the material or product made from the sheet material and provide anti-microbial properties for the entire time. It is advantageous to have the anti-microbial agent only at the surface since this is the only place where it comes into contact with microbes and fungi and to have the agent in other places in the multi-layer sheet material is wasteful.

Figure 17:
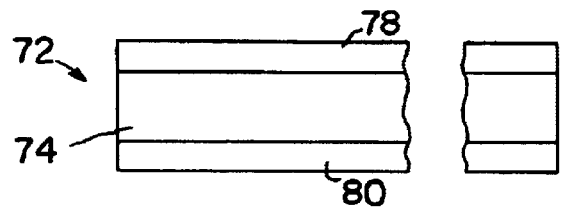
FIG. 17 is a side view of a sheet material having two anti-microbial films extruded thereon, one on each side.

Another type of multi-layer sheet construction, which may be used to accomplish the purposes of the present invention is shown in FIG. 17. In this arrangement the multi-layer sheet material 72 has a main support layer 74 and both surfaces thereof have surface layers 78 and 80, respectively. One or both of the surface layers 78 and 80 have the anti-microbial agent. Layer 74 is a wide sheet of material which may be extruded of thermoplastic material. It can be a rigid material or a flexible material depending upon the end use. The second and third layers of wide sheet material are attached to it by suitable means known in the art or they may be co-extruded as described below in connection with FIGS. 21–23. There is a surface layer having an anti-microbial agent (which may be or include an anti-fungal agent) is attached to both sides of the composite layers. These layers are connected by a suitable means known in the art when they are not co-extruded.

This three layer arrangement may be co-extruded at one time so that the three layers are bonded together immediately after extrusion and while the layers are still hot and prior to quenching. For a discussion of the co-extrusion process, see FIGS. 21 and 22 and the description thereof which appears below.

There are many uses which may be made of this composite, and the end use is evaluated to determine additional features which are added. For example, if the finished composite of FIG. 16 or FIG. 17 is to be formed into a shape for cafeteria trays or food trays (see FIG. 20), then only one surface layer having the anti-microbial agent is needed and the support layer is rigid to provide rigidity to the tray. The material is hard and smooth so that it may be easily cleaned yet still provide the anti-microbial effect. The food tray is die formed after the sheet is made by the co-extrusion process.

It is possible to form the three layer sheet 72 which includes the support layer 74 of at least 10 microns in thickness which is extruded at the same time as a second sheet 78 which becomes a two-layer sheet, the second sheet being 4 microns in thickness and being supported by the first layer. The extruding of both layers is done at the same time and the second sheet 78 is joined to the first sheet 74 before the quenching is complete. If desired a third sheet 80 similar to the second one, 78, can be made at the same time. The second and third sheets may have an anti-microbial agent of the type discussed herein mixed with the thermoplastic material so that the three layer sheet has a thin top layer and a thin bottom layer which possess anti-microbial properties.

Figure 18:
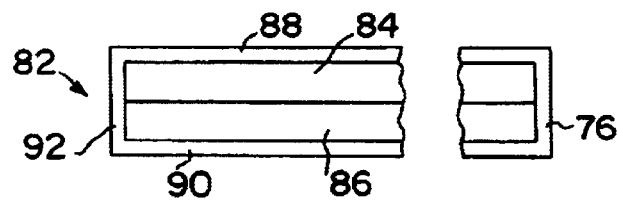
FIG. 18 is a side view of a further arrangement in which a double sheet material is complete surrounded by an anti-microbial film.
Figure 21:
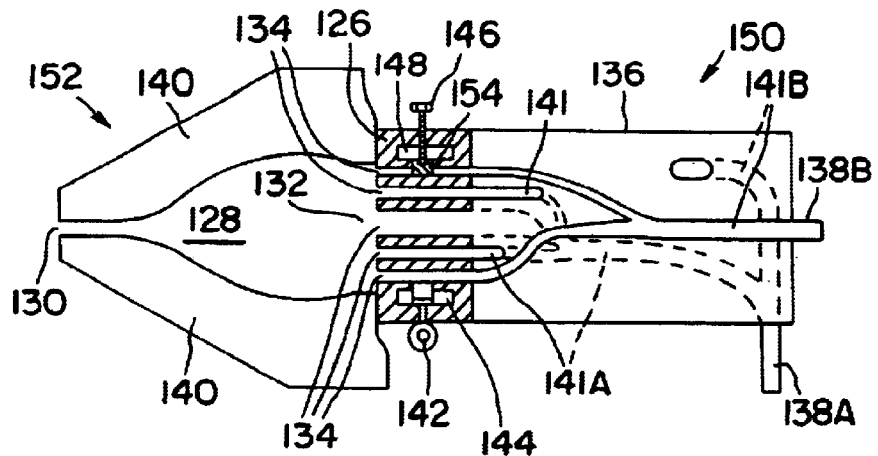
FIG. 21 is a partial sectional view of apparatus for making a multi-layer co-extruded sheet.
Figure 22:
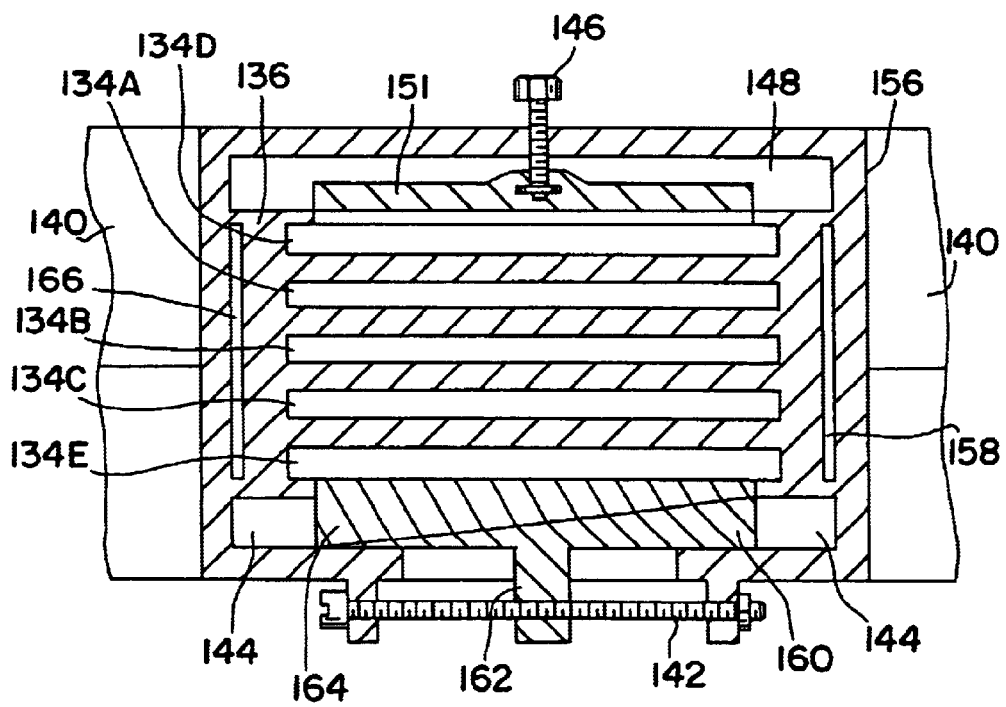
FIG. 22 is a sectional view through the apparatus shown in FIG. 21.

FIG. 18 shows a multi-layer sheet 82 having a first inner layer 84 and a second inner layer 86 with two surface layers 88 and 90. It also includes edge layers 92 and 76, and which is suitable for various purposes. It may be constructed as shown in FIGS. 21 and 22 and as described below.

Figure 19:
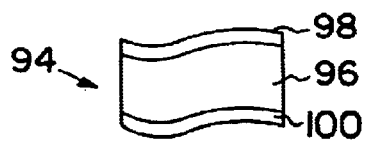
FIG. 19 is a side view of a shaped sheet material having two anti-microbial films extruded thereon.

FIG. 19 shows a multi-layer sheet 94 which has a shape in the form of a curve and which includes a center support layer 96 and two surface layers 98 and 100.

Figure 20:
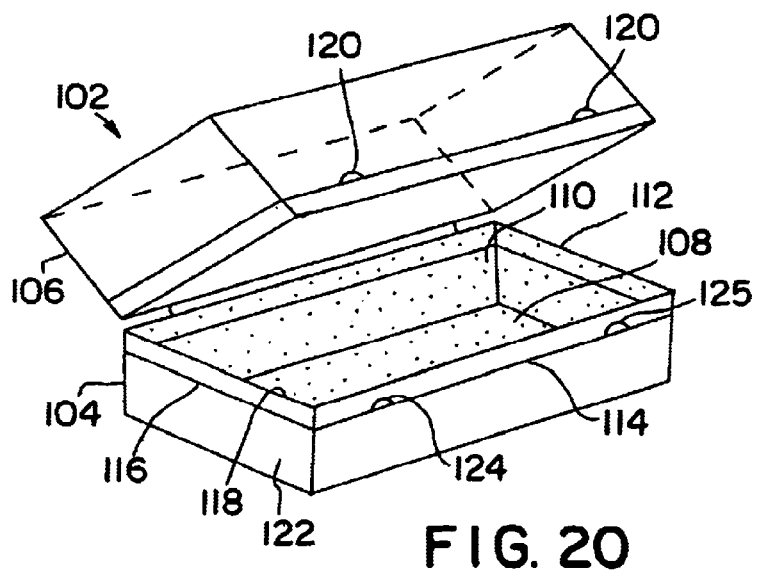
FIG. 20 is an isometric view of a food tray constructed in accordance with the present invention.

FIG. 20 shows a food tray 102 which may be the type which contains food and is purchased in food stores with food packaged therein. This tray includes two basic parts, a bottom 104 and a top 106. The bottom 104 may be of PET which is crystallized in order to provide a firm layer which may support the food products contained therein. After the multi-layer sheet material is made, the food tray parts are formed in dies. This bottom part 104 has a bottom layer 108 and four side-walls 110, 112, 114, and 116. For all the parts of the bottom 104, there is an inner layer 118 of a thin film which is attached to a support layer 122 and this film 118 contains an anti-microbial agent as indicated by the stippling. There are tabs 124 and 125 on the bottom which fit into holes 120 on the top 106. The top is made of a transparent material and is in the amorphous state. The anti-microbial agent prevents the growing of microbes which are killed upon contact with the inner film layer of the bottom of the food tray.

Making Co-extruded Sheet Material Laminates

With reference to FIGS. 21 and 22, a suitable die has a funnel-shaped expansion chamber 128 terminating in a slotted die outlet 130 defined by a pair of spaced die lips. The die has a shallow chamber entrance section 132.

The feed block 126 comprises a plurality of slotted layer distribution passages 134 in the form of mutually spaced apart slots or openings lying substantially parallel to slotted die outlet 130. The passages extend from an inlet side to an outlet side of the feed block 126.

The feed block further comprises end encapsulation slots 166 and 158 extending between inlet and outlet sides without intersecting passages 134 and lying substantially perpendicular thereto. Otherwise, slots 166 and 158 may extend along planes converging together from the inlet side to the outlet side. The feed block assembly 152 includes a frame 136 connected to the upstream end of the die in some suitable manner and defining a chamber (not shown) open on opposite sides to facilitate removal and replacement of feed block 126 with an interchangeable feed block designed to accommodate specific resin viscosities, selected polymer matchups, layer thickness changes, layer geometry, etc.

Frame 136 includes various connectors 138A and 138B to which extruders (not shown) of polymer melts are connected, and to which feed channels or feed lines (also not shown) are likewise connected for feeding the melts to slots 134A–134E, 166 and 158, or to selected ones thereof.

The feed block may be connected in some suitable manner to frame 136 or may be unconnected thereto.

Apparatus generally designated 152 is illustrated in FIGS. 21 and 22 as comprising a slit die 140 of mating die halves. A feed block assembly, generally designated 150, is totally integrated into the die as it is inserted within a die cavity 156 open at the upstream end of the die and at opposing sides of the die, shown in FIG. 21. Feed block assembly 150 comprises feed block 126, connectors 138A and 138B and melt feed lines 141A and 141B, respectively, extending from the connector 138A for feeding plastic melt from the extruder to the slotted passages 134A, 134B and 134C, and from the connector 138B for feeding plastic melts from the extruder to the slotted passages 134D and 134E. When an anti-microbial or the like is to be provided in the thinner outer sides of the sheet material, such an agent is added into the melt which is then extruded and fed to feed line 141B and connector 138B to extruding slots 134D and 134E. In the event the edges of the laminated sheet material is to differ from the material fed into feed lines 141A and 141B, a third feed line (not shown) can be connected to slotted passages 166 and 158 of the feed block. If the edges are not to be different the slotted passages 166 and 158 are not or may be omitted from the construction of feed block 126. Thus, the entire feed block assembly 150 can be removed from cavity 156 and replaced by another feed block assembly for a new production cycle.

Feed block 126 of apparatus 152 can be provided with externally accessible means to control the melt streams of polymer melt passing through the outermost slots 134D and 134E for adjusting the distribution of the outer or skin layers of the skin laminate to be formed. Such control means may be in the form of a restrictor bar 154 extending transversely to the direction of flow of melt through the passages for controlling the width and/or shape of the outermost passage upon manual manipulation of an adjustment screw 146. The restrictor bar may be located in a side cavity 148 of the feed block.

Otherwise, the skin layer control means may be in the form of a driven wedge 164 mating with a drive wedge 160 connected to a screw drive 142 via flange 162, as more clearly shown in FIG. 22. The wedges may be housed in a suitable side cavity 144, and a turning of screw drive 142 shifts wedge 160 along the screw drive and causes the driven wedge to be shifted transversely relative to the melt flow through the feed block for controlling the distribution of the skin layer flowing through the outer-most passage of the feed block.

Restrictor bar 154 can be utilized on both sides of the feed block, and the wedge arrangement can likewise be utilized on both sides. Restrictor bar 154 and wedge 164 can have flat melt flow engaging surfaces, or these surfaces can be concavely or convexly shaped or otherwise contoured to control the layer distribution of the skin layers by modifying the outer slots to accommodate differences in melt viscosities, etc.

With this arrangement one or both outer layers may have an anti-microbial agent. If a three-layer arrangement is made it can have a center layer of $10\mu$ and the outer layers may be $4\mu$. In such an event the particle size may be about $1.5–2\mu$. If zeolite of silver particles are used and made this size then substantially every particle of zeolite will have at least a portion exposed by projecting through the outer surface of the layer in which it is embedded.

Figure 23:
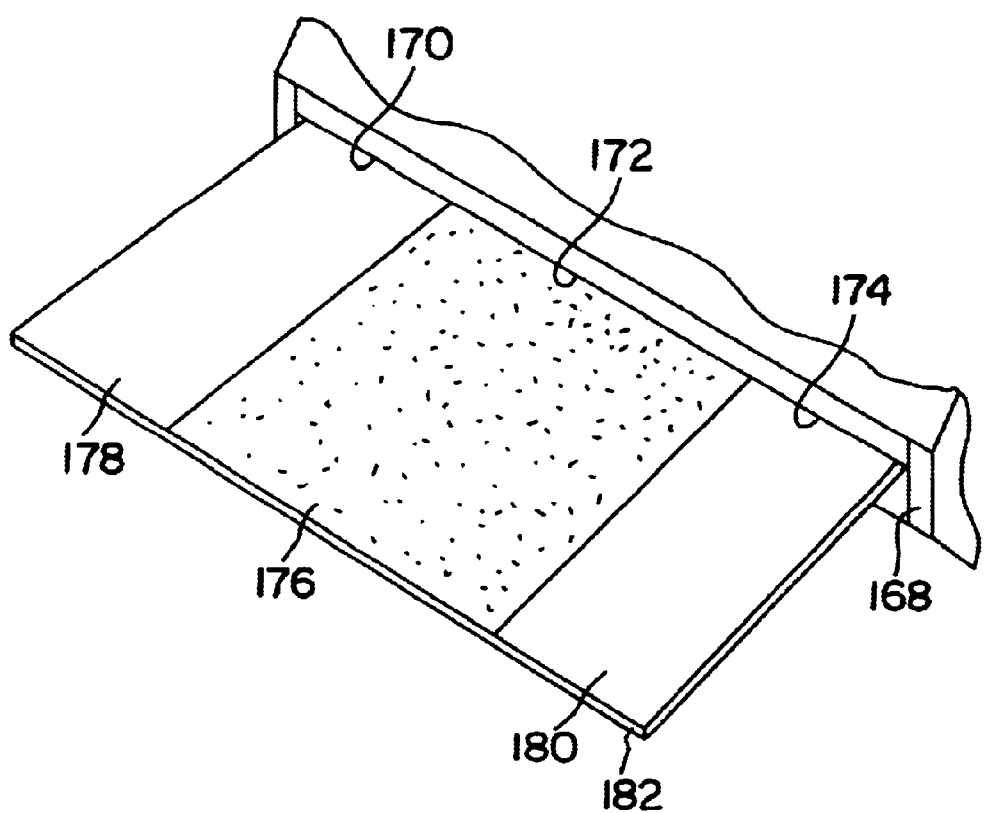
FIG. 23 is an isometric view of apparatus for making a side-by-side co-extruded sheet.

FIG. 23 shows a die 168 having a single extrusion slot with three portions, 170, 172 and 174. The sheet which is extruded thereby is shown having a center section 176 and two edge portions 178 and 180. The width of the center portion 176 is the same as the widths of the edge portions together. When the extrusion process takes place die slot portion 170 produces edge portion 178, die slot portion 172 produces center portion 176 and die slot portion 174 produces edge portion 180. The stippling indicates that an anti-microbial and/or an anti-fungal agent has been incorporated into the center portion of the extruded sheet. The extruded sheet is shown having a thickness 182 which is the same throughout, although portions could be of different thickness if this is desired.

Thus FIG. 23 shows a manner of making a co-extrusion multi-layer sheet in which the edges 178 and 180 of the extruded sheet are different from the center 176 in some respect and if desired, after extrusion and while still having the heat of the extrusion (prior to quenching) the two edge portions 178 and 180 are folded under to provide a layer under the center section. In this manner a two-layer sheet is formed with layer 176 having microbe and fungus killing properties on one side of the two-layer sheet.

If desired, the die and sheet could have only two sections of equal width, in which event one would be folded over the other to form the two-layer sheet with one layer having anti-microbial properties.

Construction of the Multi-layer Sheet Material

Anti-microbial agents can be used in making sheet materials for a variety of applications in which it is necessary or desirable to reduce bacterial and fungal growth and their resultant odor.

In manufacturing these materials, any of the embodiments described above could be used. Both the strength and resiliency of these materials is important. Any number of shaped designs could be used as appropriate. In some instances, round would be appropriate whereas in other instances rectangular or other shapes, both simple and complicated would be appropriate, all depending upon the use to be made of the material.

Also, other modifications of the characteristics of these materials beyond that of adding anti-microbial agents, including the addition of agents to increase or decrease hydrophobicity, is useful. In addition, anti-odor additives may be particularly useful in cafeteria or other types of food trays.

The relatively small size of the preferred anti-microbial agent which is silver-containing zeolite compounds (which can be as small as 2 microns and less) that are used in the manufacturing of the sheet film allow these anti-microbial agents to be incorporated into the thin sheet films instead of being applied to them. Thus, because these anti-microbial agents are an integral part of the film, they are not washed or easily abraded away and the finished articles manufactured from them are able to withstand significant wear and multiple washings while maintaining their anti-microbial effectiveness. In the case of products which are thrown away after use, the resistance to washings is not an important factor.

Specifically, higher loading of the anti-microbial agents (up to 5 times) is used to more effectively act against fungi. This higher loading may be achieved by using various zeolites followed by heating the film polymer, e.g. PET, to between 180 and 230 degrees Fahrenheit in hot water which allows further metal loading or ion exchange to replace resident metal ions with another ion or mixture of ions. In addition, this would allow the zeolite at or near the surface of the film to be preferentially loaded with the metal ion or mixtures thereof that has the desired biological effect. These methods are particularly useful in reducing costs when expensive metal ions, such as silver, are used in these processes. Also, by adding certain metals, e.g. silver, at this point in the process and not having it present during the high temperature film extrusion process, any yellowing or discoloration due to oxidation of the metal ion or its exposure to sulfur and halogens would be greatly reduced.

The synthetic films used in the present invention can be made of various polymers and co-polymers, including thermoplastic ones. These polymers include, but are not limited to, polyethylene (PE), polypropylene (PP), poly 1,4 cyclohexylene dimethylene terephthalate (PCT), PET, PET type G (PETG), co-PET, and co-polymers generally. These films can also contain styrene, Halar®, and various polyamides.

As defined in this invention, anti-microbial means a thousand-fold reduction in bacteria. Thus, the materials and products of this invention are subjected to tests which show a 1000-fold reduction in colony forming units (CFU) of bacteria. To kill bacteria means a ten thousand-fold reduction in bacteria and the materials and products of this invention are capable of a 10,000-fold reduction in CFU of bacteria.

This level of antibacterial protection is achieved generally by having between 0.1 and 20 percent by weight of an anti-microbial agent incorporated into a multi-layered sheet material. Alternatively, the anti-microbial agent concentration can be reduced to between 0.2 and 6.0 percent in multi-layer sheets in which the anti-microbial agent is only mixed into the outer layer(s) of the multi-layer sheet. This latter configuration allows less anti-microbial compound to be used, thus significantly reducing the cost of manufacture, and thus the cost of the sheet material.

It is also possible to use these integrated anti-microbial compounds to make sheet materials and products that have a varying distribution of the anti-microbial agent. For example, by varying the concentrations of the anti-microbial agent during mixture with the film-forming polymers, films having varying anti-microbial content can be formed which can then be added in varying amounts to form sheet materials having varying concentrations of anti-microbial agents. In addition, the amount of anti-microbial present in the film itself can be varied, either lengthwise or in cross-section. Similarly, higher and lower concentrations of these anti-microbial agents in the overall films can be achieved by using multi-layered sheets in which, for example, the anti-microbial agent is present only in an outer layer section, thus significantly reducing manufacturing and selling costs. Any of the above manufactured anti-microbial films can be used with films that do not contain anti-microbial agents such that sheets and products can be made having overall and localized variations in concentrations of anti-microbial agents.

Color pigments can be added to these anti-microbial films in order to provide a pleasing coloration for such sheet materials when the ultimate products are purchased by consumers. Similarly to the above anti-microbial agents, these pigment materials can be added such that the pigments are encapsulated in the polymers that are used to make these sheet materials. By using this method of coloring the films, materials for end use products made from these colored films are color-fast and do not leach out their color during washing, thus significantly reducing fading during use and washing. In addition, since the need for conventional dyeing techniques can be reduced or eliminated, the disposal of environmentally damaging dye materials is avoided. This, in and of itself, can reduce the costs of manufacturing finished colored sheet materials due to the elimination of the manufacturing infrastructure and associated personnel needed to process residual dye effluents.

In a similar fashion to anti-microbial agents and color pigments, a variety of other additives that are used for various purposes can be combined with the polymers during or after film formation and extrusion. For example, additives that protect against damage from UV light can be added to the film polymer or coated onto it so that the sheet materials or end use products formed are resistant to the fading of colors and UV damage generally, although this is not a factor for all products. Both flame-resistant and -retardant agents can also be added to the films of this invention in a manner similar to that described for UV protecting agents. In this way, the sheet materials formed can be made resistant to fire.

In addition, the films can be made either hydrophilic or hydrophobic as desired by mixing other agents into the film polymers or applying them to the film surface. By modifying the wetability characteristics of the films, they can be made more useful for various applications. For example, hydrophilic films are effective in applications in which one wants the anti-microbial sheet material to more easily absorb water, such as when the material is designed to be used in humid conditions. Alternatively, hydrophobic films are effective in applications in which one wants to avoid the absorption of such solutions.

The anti-microbial agents can also be added to low-melt polymer films that can be activated and melted during sheet material production by raising the temperature, thus spreading the anti-microbial agents throughout the material when the low-melt films melt and coat the surface of the supporting layer. By varying the amount of anti-microbial-containing low-melt film regionally and/or by varying the amount of anti-microbial agent in these low-melt films, a sheet material can be produced that has a purposely designed regional variation in anti-microbial effectiveness throughout.

Specifically, the latter situation can be achieved by using an amorphous binding film such as PETG, which can be blended to form various types of sheet materials. After heat activation, the PETG melts, wetting the surface of the surrounding films adjacent surface or surfaces. In this way, solidified PETG forms and binds the layers together while spreading the anti-microbial agent throughout the surfaces. Because of the excellent wetting characteristics of PETG, the anti-microbial agent can be uniformly distributed throughout the material. These methods of activating PETG may also be used to additionally distribute other additives described above throughout the finished materials.

The anti-microbial additives used are metals such as copper, zinc, tin, and silver as part of an inorganic matrix. The best results can be obtained using a zeolite of silver dispersed in a PE,PP, PS, Nylon, PET, or PBT carrier. These additives can be added directly to the melt without a carrier. The total anti-microbial additive concentration ranges from 0.2 to 6.0 percent by weight of fiber depending on performance requirements. Other additives which can be incorporated include one or more of UV stabilizers at 0.1 to 5.0 percent; fire-retardant additives at 0.1 to 5.0 percent; pigments at 0.1 to 5.0 percent; hydrophilic additives at 0.2 to 5.0 percent; and hydrophobic additives at 0.2 to 5.0 percent.

Another configuration of the present invention is a multi-layered film in which the components are the same polymers and additives as described above. In this embodiment one layer is used for strength another layer is used as a binder that contains inserted additives. Variants of this such as three and four layered products, and even up to ten layered products with the outer two layers carrying the anti-microbial agent can also be made.

It should be understood that the nominal binder or binder component can also be a strength enhancer in some combinations. It will also be understood that other variants including but not limited to combinations, can be made. For example, a first extrusion could produce intermediate film products and such products could be put together with each other or with separate layers.

Another embodiment is a grouping of layers used to practice the invention. One configuration uses PET or other high tenacity polymer at between 20 and 80 percent by weight. Poly 1,4 cyclohexylene dimethylene terephthalate (PCT) or other hydrolysis resistant polymer is used in another layer at a ratio of 80 to 20 percent. One layer is designed to provide the strength and the modulus can be varied to create a high modulus layer, or a low modulus layer, or anywhere in between. The use of PCT in the a layer provides a hydrolysis resistant surface and resistance to long term washings in boiling water and strong soaps. The multi-layer anti-microbial/anti-fungal synthetic layers can be produced in a wide range of thicknesses.

Additives include pigments, compounds to create a hydrophilic surface, and anti-microbial, anti-fungal, and anti-odor agents. The pigment additives provide uniform colors that do not fade significantly over long-term use and washing, unlike dyes, because these additives are integrally mixed within the polymer making up the sheet or film. In addition, compounds may be used which create a hydrophilic surface. The anti-microbial, anti-fungal and anti-odor additives can be varied, both in types and amounts, depending on the final product desired.

One layer made from low temperature polymers with a melting or softening temperature below 200 degrees C., such as PETG, PE, PP, co-PET, or amorphous PET, may be used as binder carrier for anti-microbial additives.

The anti-microbial additives are inorganic compounds of metals such as copper, tin, zinc, silver, etc. The preferred compound is a zeolite of silver dispersed in PE, PET, or PBT before being added to the layer. The additives could be added directly to the primary polymer with pre-dispersion. The total active ingredients range from 0.1 to 20 percent by sheet weight.

Thus, an anti-microbial sheet material can be produced that is able to withstand significant wear and washings and maintain its effectiveness.

OFFICE PARTITION AND OFFICE COMPONENT FABRICS

89. Office partition and office component fabrics, an example being shown in FIG. 27 which is a cross section through an office partition in which there is a multi-layer partition having a filling layer 240, a fabric layer 242 on one side and a third layer 244 which may also be of fabric or can be of a solid material. Office type partitions walls can be portable or semi-portable divers of open area for personnel work stations and other assigned work and waiting areas for employees and clients. The fiber can be wholly or partly synthetic fibers which is mono-or multi-component and can be used with other synthetic or natural fibers to form a variety of fabrics uses as wall covering and/or wall fillers. Partitions of this type are used in office factory, storage and customer service areas. They are provided with fabric surfaces (woven, knits, or non-woven) for aesthetic reasons, sound absorption and/or to cushion impacts. They may also be divided with internal fabric or loose fiber fills for cushioning, wall covering substrate support and sound and/or thermal insulation purposes. The anti-microbial agent is incorporated into the fibers in one or both of the outer layers 240 and 244. This can include fabrics for office, hospital, waiting area, classrooms, busses, cars, and the like and also curtains, upholstery, carpets and bedspreads. In addition to the anti-microbial agent, other materials can be added to the fibers such as pigments, fire retardants, color fixing agents, and UV resistant agents. Partitions are assembled, disassembled, moved and reassembled with some frequency. This and traffic around such partitions creates an environment for spread of airborne or contact transmitted disease, and partitions are frequently touched. This invention provides partition systems and other articles of the type described. An anti-static agent can be added to assist in dissipating static charges which create problems, for example, when computers are being used. The product remains intact when subjected to normal cleaning and can be assembled by being needle punched, resin bonded wet laid, thermo-bonded, and spun bond. In office environments there is the spillage of food and spills from office supply and janitorial materials and simple hand contact on wall surfaces. These and other environmental insults have the potential to leave residues that can be good substrates for the growth of bacteria, mold and other microbes. They can be in moist environments and the partitions are site for growth, and also from airborne microbes.

CAR WASH MATERIALS

Car wash materials, including shami type materials, in which the anti-microbial features last for the normal life of car wash cloths, for example, from 6 to 9 months. In car washes, many types of fabrics are used in the washing process. For instance, the automatic machines that wash cars use a variety of shaped fabrics to clean the car. In addition, cloths of various kinds are used in the waxing, dying, and finishing processes. Due to their continual contact with water, which itself is often recycled, these materials are often wet for long periods of time. This type of situation is very favorable to the growth of bacteria, fungi, and other microbes. As a result of the above, the use of anti-microbial fibers in the manufacture of materials used to clean cars in car washes is a desirable goal. These anti-microbial fiber-containing materials are useful in materials used by the automatic machinery and by individuals employed to clean the cars as well as in other ancillary materials. Specifically, the shaped fabrics used for automatically cleaning the car and the hand towels used to wax, dry, and otherwise finish the car are better products when these anti-microbial fibers are added to them. In manufacturing these materials, any of the embodiments described above could be used. Both the strength and resiliency of these materials is important given that they are used multiple times and are subject to being constantly in contact with water. Thus, both bi-component fibers and mixed fiber fabrics are useful embodiments for car wash materials. Also, other modifications of the characteristics of these fibers and fabrics beyond that of adding anti-microbial agents, including the addition of agents to change the hydrophobicity, are useful in view of their constant contact with water. Thus, these anti-microbial materials that are manufactured to be used in car washes significantly reduce the growth of mold, mildew, and bacteria. By achieving this goal, odors associated with the long-term use of these materials is reduced. Also, the number of times they can be re-used before being discarded is increased, both because of the incorporation of anti-microbial fibers into these materials and the strengthening strategies indicated above. These characteristics also result in a significant costs savings in the operation of car washes. The hydrophilic and anti-microbial additives provide a hydrolysis-resistant surface that results in long-term protection against washings in boiling water and strong soaps, and also degreasers and chemical based cleaners. The anti-microbial synthetic fibers can further be blended with non-anti-microbial fibers such as cotton, wool, polyester, polypropylene, acrylic, nylon and the like, to provide anti-microbial finished fabrics that are able to withstand significant wear and washings and while maintaining their effectiveness;

CAR WASH WATER FILTERS

91. Car wash water filters are more useful when the anti-microbial fibers are used in the making of such filters. Also batts and "brillo" type pads can be used which float, or are submerged in a recycled water storage tank, and the anti-microbial fibers included in them kill the microbes, which are in the tank. This is especially important in car washes, which recycle the wash water, which is the majority of car washes. In car washes, the water that is used to wash the cars and the associated materials for performing the washing and drying operations is often recycled water. However, there are several disadvantages to using recycled water. These include the dirt and odor-causing materials found in the water, including various bacteria, fungi, and other microbes. Because of the use of recycled water, very favorable conditions exist for the growth of bacteria, fungi, and other microbes. As a result of the above, the use of anti-microbial fibers in the manufacture of filter materials used to clean the recycled water before re-use in car washes is a desirable goal. These anti-microbial fiber-containing filters are useful in reducing the build-up of biological materials and films, both on the machinery employed to clean fabrics and other materials associated with the car wash process, due to the recycled water re-use. Specifically, the shaped fabrics used for automatically cleaning the car and the hand towels used to wax, dry, and otherwise finish the car are less prone to the development of bacterial and fungal films. They are also less likely to impart undesirable odors to the car itself. In addition, the recycled water itself would be less likely to impart any odors to the car. They assist in improving the air quality for customers as they drive through a car wash, and also for the employees. In manufacturing these materials, any of the embodiments described above could be used. Both the strength and resiliency of these materials is important given that they are used multiple times and are subject to the high pressures characteristic of filtering processes. Any number of filter shape designs could be used as appropriate to the step in the filtration that was being performed. In some instances, round filters would be appropriate whereas in other instances pleated or other shape filters would be appropriate, all depending on the pressure and volume characteristics of the recycled water flow. Also, the batts mentioned above can be used in the recycled water storage tanks or sumps to assist in cleaning the water by killing microbes and fungi. Anti-odor additives may be particularly useful in this application given the use of recycled water. Thus, these anti-microbial car wash filters and batts significantly reduce the growth of mold, mildew, and bacteria in the recycled water and on car wash materials. By achieving this goal, odors associated with the long-term use of recycled water and these materials would be reduced. Also, the number of times the recycled water and the car wash materials could be re-used before being discarded could be increased. The ability to re-use recycled water several additional times because these types of filters and/or batts are employed in the recycle process would results in a significant costs savings in the operation of car washes;

INSTITUTIONAL PRODUCTS AND HOME FURNISHINGS

Institutional products and home furnishings, such as bed sheets, pillow cases, mattress pads, blankets, towels, drapes, bedspreads, pillow shams, carpets, walk-off mats, napkins, linens, wall coverings, upholstered furniture, liners, mattress ticking, mattress filling, pillow filling, carpet pads, upholstery fabric and the like, are significantly improved when made using, at least in part, the anti-microbial fibers described above. Further details of these institutional products and home furnishings are provided below; Mattress pads ½" to 1" in thickness are made, for example, as set forth in Example 1 above. The web can be air laid and the binder fiber melts in an oven. Thus, the sheath is melted and spreads on the other fibers. 5% of the fiber blend mass can be anti-microbial fiber. The entire sheath is anti-microbial fiber.

Bed sheets and pillowcases can be made of anti-microbial fiber. They can be constructed using low melt binder fiber blended in at levels of 1 to 20%. The binder fiber can be blended with other fibers such as cotton, wool, polyamides, viscose, flax, acrylic, or polyester. The low melt binder fiber contains levels of the active anti-microbial ingredient ranging from 0.25% to 5%. Fiber properties are from 0.7 denier through 25 denier with cut lengths ranging from 1 mm to 180 mm.

The bed sheets and/or pillowcases can also be constructed using the bi-component sheath/core polyester fibers with the active anti-microbial ingredient in the sheath only.

The anti-microbial fibers are used to spin yarn in cotton counts ranging from 4's to 80's. Sheets and pillowcases may be woven or knitted. Yarns used to weave the bed sheets/pillowcases, containing the anti-microbial treated fibers, may be used only in the warp direction, or the filling direction, or may be used in both.

Some sheets and pillowcases have been made using 1–15% anti-microbial fiber in the fabric, which are 1.5–3.5 denier, 1½" staple length and in which 15% of the filling yarn is anti-microbial. For example, they can have 15% anti-microbial fiber, 35% cotton and 50% untreated polyester.

PETG is blended with the cotton, and is heated, it does not ball up but wicks along the other fibers. The cross section becomes thinner as the PETG flows. For loose knit fabrics 15–20% anti-microbial fiber is useful to kill the microbes, whereas for flat woven fabric there can be 10% or less anti-microbial fiber to kill microbes.

The same fabric can be used in bed sheets and for medical scrubs. Woven fabric is desized to remove starch from the warp yarns. High loft batting is used to stuff the mattress pad. 15% of fiber blend is bi-component. In one example, the fiber was made with all PET sheath and core, and was 6½ oz per square yard, 6 denier blended with 6 denier regular while.

Anti-microbial Products for Institutional and Home Furnishings

Institutional and home furnishings include a variety of items such as bed sheets, pillow cases, mattress pads, blankets, towels, drapes, bedspreads, pillow shams, carpets, walk-off mats, napkins, linens, wall coverings, upholstered furniture, liners, mattress ticking, mattress filling, pillow filling, carpet pads, upholstery fabric, and each of these have different requirements depending upon their intended use. While topical applications of agents have been used in the past they do not stand up to wear and to repeated launderings. Therefore, the present invention provides for the addition of such agents, such as anti-microbial agents at the fiber making stage of manufacture and prior to the fabric or material or product being prepared.

Bed Sheets and Pillow Cases

These will usually have the same requirements and be prepared in a similar manner. Fibers and yarns have been prepared to have anti-microbial properties and then are used to make bed sheets and pillow case material which is then made into the final product.

Mattress Pads

The anti-microbial fibers are used for the top and bottom layers of the pads which are sealed or connected to each other along their perimeters. This can be by sewing with thread or in some other suitable manner. The center is filled with a batting material which includes 15% anti-microbial fiber produced as described below. The top and bottom layers are woven fabric which is made from yarn which contains 15% anti-microbial fiber produced as described below.

It has been found that when these fabrics are dyed, the dyeing process can have the effect of blocking the anti-microbial action. However, in accordance with the present invention this problem is resolved by using hot water soaks or washes which rejuvenates the fiber's anti-microbial agents.

Anti-microbial fibers can be used to make materials for a variety of applications in which it is necessary or desirable to reduce bacterial and fungal growth and their resultant odor. Specifically, in institutional environments, these materials can be used in support substrates for furnishings. In these situations, these support materials are subject to a variety of environmental insults that can cause the growth of bacteria, fungi, and other microbes. These include the spillage of food and its seepage inside furnishings and spills from janitorial materials. These and other environmental insults have the potential to leave residues that can be good substrates for the growth of bacteria, mold, and other microbes. Therefore, unsanitary conditions can occur along with the associated bad odor, both of which can contribute to patient sickness and allergy, a deterioration of patient morale, and sick building syndrome, in general.

As a result of the above, the use of anti-microbial fibers in the manufacture of support substrates for institutional furnishings is a desirable goal. These anti-microbial fiber-containing support substrates are useful in reducing the build-up of biological materials and films, thus reducing associated patient discomfort and environmental contamination. Specifically, the anti-microbial-fiber containing support substrates could be coated with polyvinyl chloride (PVC) or laminated to woven or knit fabrics in the construction of institutional furnishings.

In manufacturing the furnishing type materials, both the strength and resiliency of these materials is important given that they must stand up to a variety of environmental insults, frequent moves, and varying storage conditions. They must also be strong enough to act as supporting members of the furnishings themselves. Thus, both bi-component fibers and mixed fiber fabrics are useful embodiments for support substrates for institutional furnishings. Also, other modifications of the characteristics of these fibers, their associated fabrics, and support materials beyond that of adding anti-microbial agents, including the addition of agents to increase or decrease hydrophobicity, are useful given the need for frequent cleanings and washings. In addition, anti-odor additives may be particularly useful in this application given this frequency of cleaning as well as the variety and number of environmental insults to which these fabrics are exposed.

Thus, these anti-microbial materials that are manufactured to be used in support substrates for institutional furnishings significantly reduce the growth of mold, mildew, and bacteria in the institutions. By achieving this goal, odors associated with the long-term use of these materials and their frequent storage and re-use is reduced. Also, the length of time that these furnishings can be used in the office increases greatly, thus resulting in a significant costs savings in the furnishing of institutions.

Color pigments may be added to these anti-microbial fibers in order to provide the desired coloration for finished fabrics and materials. Similarly to the above anti-microbials, these pigment materials can be added such that the pigments are encapsulated in the polymers that are used to make these fabrics. By using this method of coloring the fibers, materials and fabrics made from these colored fibers are colorfast and do not leach out their color during washing, thus significantly reducing fading during wear and washing. In addition, since the need for conventional dyeing techniques can be reduced or eliminated, the disposal of environmentally damaging dye materials is avoided. This, in and of itself, can reduce the costs of manufacturing finished colored fabrics due to the elimination of the manufacturing infrastructure and associated personnel needed to process residual dye effluents.

In a similar fashion to anti-microbial agents and color pigments, a variety of other additives that are used for various purposes can be combined with the polymers during or after fiber formation and extrusion. For example, additives that protect against damage from UV light may be added to the fiber polymer or coated onto it so that the fabrics and materials formed are resistant to the fading of colors and UV damage generally. Both flame-resistant and -retardant agents can also be added to the fibers of this invention in a manner similar to that described for UV protecting agents. In this way, the fabrics and materials formed can be made resistant to fire. Anti-stain agents can also be added to the fibers or resultant fabrics in the above manner.

In addition, the fibers can be made either hydrophilic or hydrophobic as desired by mixing other agents into the fiber polymers or applying them to the fiber surface. By modifying the wetability characteristics of the fibers, they can be made more useful for various applications. For example, hydrophilic fibers are effective in applications in which one wants the anti-microbial fabric or material to more easily absorb water, such as when the fabric is designed to absorb solutions containing bacteria and fungi and other microbes. Alternatively, hydrophobic fibers are effective in applications in which one wants to avoid the absorption of such solutions, such as in the manufacture of clothing, in general, and in work clothes, in particular.

The anti-microbial agents can also be added to low-melt polymer fibers that can be activated and melted during fabric production by raising the temperature, thus spreading the anti-microbial agents throughout the fabric when the low-melt fibers melt and coat the interstitial intersections of the other fibers. By varying the amount of anti-microbial-containing low-melt fiber regionally and/or by varying the amount of anti-microbial agent in these low-melt fibers, a fabric or material can be produced that has a purposely designed regional variation in anti-microbial effectiveness throughout.

Specifically, the latter situation can be achieved by using an amorphous binding fiber such as PETG, which can be blended into yarns and with other fibers to form fabrics and materials. After heat activation, the PETG fibers melt, wetting the surface of the surrounding fibers and settling at the junctions of other heat-stable fibers. In this way, solidified drops of PETG form at these junctions and bind the fibers together while spreading the anti-microbial agent throughout the fiber. Because of the excellent wetting characteristics of PETG, the anti-microbial agent can be uniformly distributed throughout the fabric. These methods of activating PETG fibers may also be used to additionally distribute pigments and the other additives described above throughout the finished fabrics and materials.

The binder fiber carrier containing polymers and anti-microbial additives can be blended with non anti-microbial fibers such as cotton, wool, polyester, acrylic, nylon, PTT, 3GT, rayon, modified rayon, and acetate to form anti-microbial finished fabrics. Thus, an anti-microbial finished fabric is produced that is able to withstand significant wear and washings and maintain its effectiveness.

A typical example of this embodiment is a fiber using PETG polymer with a silver zeolite additive to blend with cotton at concentrations up to 10 percent by weight to produce a bed sheet. The binder fiber is activated in the drying cycle of the final bleaching operation or other heat operation. The PETG then melts and wets the surface of the cotton fibers to carry the anti-microbial property to the entire sheet with an added benefit of increasing strength and reducing pilling.

ATHLETIC WEAR

93. Athletic wear clothing and liners, including athletic wear liners made from a wholly or partly synthetic fiber that can be wither mono-or multi-component in nature, and binder fibers both staple and filament, with anti-microbial properties and which can be used with other synthetic or natural fibers to form a variety of fabrics and materials. Athletic wear is subject to the accumulation of bacteria, fungi, and associated odors that can proliferate in the presence of sweat and other bodily secretions that result from strenuous exercise in this type of clothing. This type of product may be made using anti-microbial fibers, and which for some applications are provided with a layer which touches the skin and wicks away the sweat to make a more comfortable garment (or liner) and this type of article benefits from the use of anti-microbial fibers in at least one layer. They can include T-shirts, crotch liners, bicycle pants and shirts, sweat suits, athletic supporters, stretch pants, long underwear, and athletic socks. Because this type of clothing is constantly and intermittently being soaked with sweat and brought into contact with dirt and associated materials, they are subject to bacterial and fungal growth as well as to the development of associated odors. By manufacturing this clothing with lining materials made, at least partially, of the anti-microbial fibers of this invention, growth of microbes could be reduced. In addition, the exacerbation of microbial growth and resultant odor production upon storage of this type of clothing in bags over time could be reduced. These anti-microbial fiber-containing clothing is useful in reducing the growth of bacteria, fungi, and other microbes once soaked with sweat, thus reducing associated odors and the discomfort of the individual. Specifically, the anti-microbial-fiber containing fabrics may be used in the interior linings of shirts and pants or shorts, such as those used in running and bicycling. These anti-microbial fibers may also be used in the manufacture of athletic clothing that does not have linings. This type of athletic clothing is then able to be used for long periods of time while maintaining its anti-microbial and anti-odor properties because of its resistance to multiple washings. In addition, the methods described above could also be used to produce clothing dyed in a variety of colors that would possesses the characteristics of inhibiting microbial growth and its associated odors, thus increasing its versatility;

MOP HEAD FABRICS

Mop head fabrics can be of fibers in yarns, knitted fabrics, woven fabrics or non-woven fabrics. Mop head fabrics are subject to bacterial and fungal growth due to their constantly being wetted upon use, and are left wet in storage and allowed to air-dry. This constant wetting also causes the development of odors and the eventual deterioration of the integrity of the mop head materials themselves. Mop heads can transfer bacteria and fungi from one area to another and thus can be the cause of significant collections of microbes and fungi. Thus, these mop head fabrics made from anti-microbial materials significantly reduce the growth of mold, mildew, and bacteria. By achieving this goal, odors associated with the long-term use of these materials are reduced. Also, the number of times they may be re-used before being discarded is increased, both because of the incorporation of anti-microbial fibers into these materials and the strengthening strategies indicated above. These characteristics also result in a significant costs savings in the use of mop heads in industrial settings;

MEDICAL WIPES

Medical wipes described in further detail below; Medical wipes are made using anti-microbial fibers in their manufacture. These anti-microbial fiber-containing medical wipes are useful in reducing the growth of bacteria, fungi, and other microbes that can be introduced from the environment during the cleaning of surfaces in institutional settings, thus reducing and preventing infections generally. Specifically, the anti-microbial-fiber containing fabrics may be used in both the covering fabric and the water absorbent interior material. In this way, both surface and interior protection can be achieved. In addition, these materials could also be manufactured as reusable wipes because the anti-microbial effect of the fibers of this invention are resistant to multiple washings. Thus, a significant cost savings could be realized in the purchasing of supplies in a variety of institutional settings, including hospitals and nursing homes.

The finished product may be constructed of nonwoven, knit, woven or other process. It may also be treated or pre-moistened with a topical treatment such as a soap solution or other additive. The finished product can be produced from any combination of natural or synthetic fiber in addition to the anti-microbial fibers. The wipe cloth may be unitary or combined or laminated to some other fabric.

In manufacturing these materials, any of the embodiments described above or below can be used. Both the strength and resiliency of these materials is important given that they must withstand the cleaning of multiple surfaces. Thus, both bi-component fibers and mixed fiber fabrics are useful embodiments for medical wipes. Also, other modifications of the characteristics of these fibers and fabrics beyond that of adding anti-microbial agents, including the addition of agents to increase or decrease hydrophobicity, are useful in manufacturing sturdy medical wipes. Also, anti-odor additives are useful in this application given the exposure of the wipes to a variety of biological and chemical environmental contaminants. Thus, these anti-microbial materials can significantly reduce the growth of mold, mildew, and bacteria in medical wipes.

In one multi-layer embodiment, there is a skin contacting layer which contains the anti-microbial fibers, an absorbent layer adjacent to the first layer and which contains a cleaning solution, a non-permeable layer adjacent the absorbent layer to prevent the user being contacted with the solution or by any of the products from a wound, and a tab attached to the non-permeable layer as a handle for the user.

DUST MASKS

Dust masks are vulnerable to the capture and seeding of bacteria and fungi. They can provide hospitable sites for the protected growth and the inhalation/exhalation of microbes. These products benefit from having anti-bacterial and anti-fungal agents incorporated into them. Dust masks may be of a nonwoven construction of anti-microbial fibers (at least in part) and may be covered on one or both sides with a fabric layer. Such masks which can have or provided anti-microbial containing filters are useful in reducing the build-up of biological materials on the dust mask which could be inhaled by the user. Both bi-component fibers and mixed fiber fabrics are useful embodiments for dust masks. Other agents may be used as disclosed herein;

FIBROUS MEDIA

Figure 29:
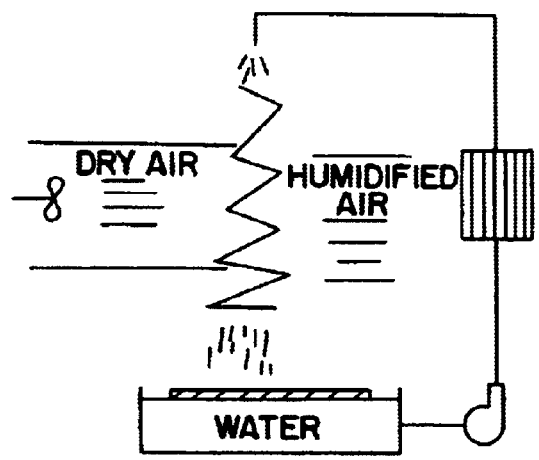
FIG. 29 is a schematic view of a humidifier pad or filter in a system.
Figure 30:
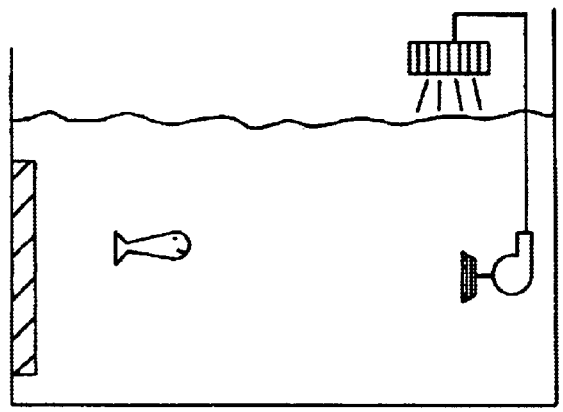
FIG. 30 is a pad or filter for a circulation/aeration system.

Humidifier evaporation surface media introduces an anti-microbial fiber into the evaporation surface media for humidifiers. Such a media prevents the growth of mold, mildew, bacteria, and fungi on the media. Preventing such growth reduces or eliminates the "musty smell" currently experienced when such devices are started up to humidify home or office environments. It reduces or prevents the growth of organisms in humidifier systems to prevent odor and bacterial growth. The media may be made of a non-woven fibrous material made at least in part of the anti-microbial fibers disclosed herein. FIG. 28 is a schematic view of a humidifier evaporation surface media, which is made at least in part of anti-microbial fibers, used to humidify air. FIG. 29 shows a humidifier pad which could float on the surface of a tank, be attached to the bottom or sides of the tank, or in the suction or discharge sides of the circulation pump, and it is made at least in part of the anti-microbial fiber disclosed herein. FIG. 30 shows a "fish tank" circulation/aeration system. An anti-microbial pad or filter is on the suction or discharge side of the pump or attached to the bottom on the sides of the tank. This helps prevent the growth of microbes in recirculation systems and tanks which can not use chemicals or in which it is desired not to use chemicals. This and other uses for anti-microbial fibers in different environments show that a person working, for example, in a moldy or dirty environment would want as much assistance as possible in a respirator or filter or mask. Also, one wants the anti-microbial agent to remain in the fiber and not be inhaled by the user.

BOAT BILGE PADS

98. Boat bilge anti-microbial pads can be made at least in part with anti-microbial fibers can be used in a filter in the system or can be used in a manner similar to that of the car wash filter in pads which are placed into the water storage tank to kill bacteria in the water;

LAUNDRY BAGS

Laundry bags can be made at least in part of anti-microbial fibers as described herein to reduce odors and to kill bacteria which may be present in the bags;

APPAREL

Apparel can be made using anti-microbial fiber as described elsewhere herein;

INSOLES

Figure 24:
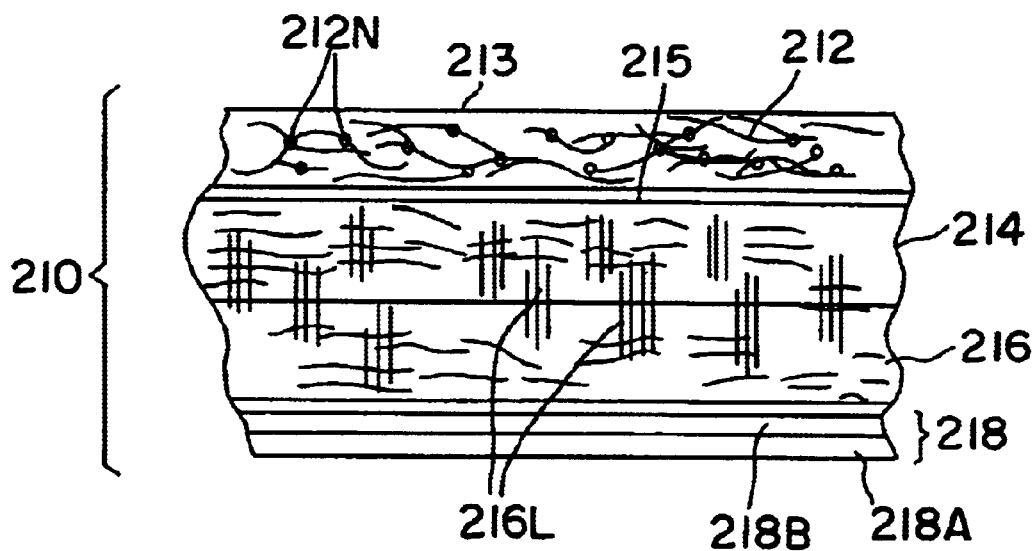
FIG. 24 is a cross section through an insole made in accordance with the present invention.
Figure 25:
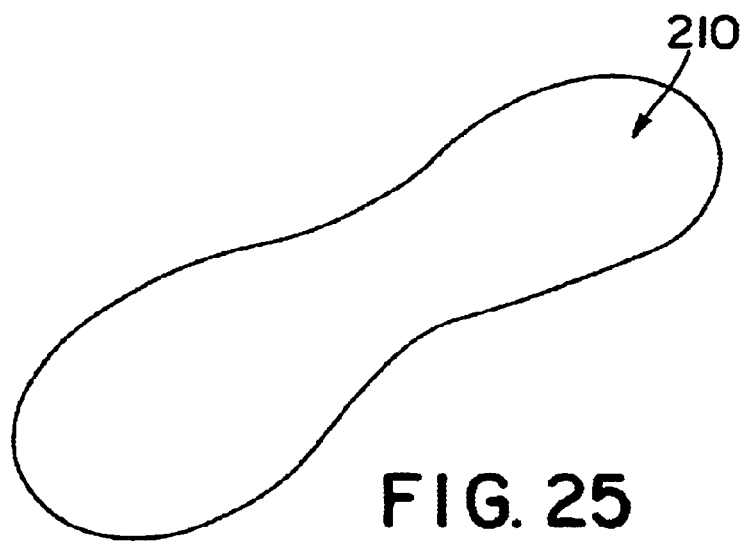
FIG. 25 is a plan view of the insole of FIG. 24.

Insoles are described in more detail below; A further embodiment of practice of the invention is shown in FIGS. 24 and 25 wherein an insertable innersole 210 for shoes and boots is made up of multi-layers indicated in FIG. 24. The layering is indicated before heating and pressing this laminate to form a bonded construction. The innersole has anti-microbial that are available in the as fully manufactured product and, as in other embodiments of the invention described above, are provided in a cost efficient way.

A top layer 212 of the laminate is made of a non-woven or woven array of fibers, preferably of polyester, has an overall weight of 2.5 to 6.0 oz. per square yard and includes some 5–25% of its weight as fibers that are mono-component or multi-component and incorporate zeolites of silver or other anti-microbial dispersed substantially uniformly in the layer. In eventual processing the surface 213 gets treated by embossing, ultrasonic bonding and/or other modification and the layer as a whole is heated (along with heating and pressing the laminate as a whole) to effect, among other things, bonding of fibers at many cross over points (nodes) 212N in a manner well known in the art to effect densification and strength while retaining substantial porosity and moisture vapor permeability through the layer.

The next major layer 214 is made of thermo-formable polymers, preferably polyesters and/or co-polyesters including 20–80 weight percent of mono-component fibers and conversely 80–20 weight percent of multi-component fibers, the latter incorporating anti-microbial agents as described herein, the layer weight in 2.5–9.0 oz. per square yard. The layer is non-woven needle-punched fabric with some distinct fiber orientation in the lateral direction within layer 214 itself and with punched through fibers from the next lower layer as described below. This layer 214 is bonded to layer 212 by a an adhesive web of scrim or mesh form of 15–30 gm per sq. meter weight (very diaphanous) and made of polyester, polyolefins (polethylene, polypropylene, etc.), polyamide or other fiber materials and in the course of laminate heating and pressing becomes an effective bonding agent to bond layers 212, 214 securely to prevent delamination in service use.

The next major layer 216 is designed as a moisture storage (and eventual off-gassing) layer with high surface area fibers, including 20–50 weight percent of 4DG lobed or grooved fibers of polyester or other fiber material of a type well known per se, 50–60 weight percent of normally surfaced polyester mom-component fibers and 5 to 25 weight percent of bi-component fibers containing anti-microbial agents. The bi-component fibers are preferably normally surfaced but could also be made of grooved form, consistent with the missions of anti-microbial agent carriage and access. The layer as a whole weighs 4–12 oz. per sq. yard and is bonded to layer 214 by deep needle-punching fibers of layer 216 into layer 214 using barbed felting needles to establish lateral wicking paths as indicated, e.g., at 216L.

The final layer 218 is a co-extruded two part plastic film with a barrier sub-layer portion 218A and a bonding sub-layer portion 218B, each such portion being 25–100 microns thick and made of A/B combinations of, e.g., polypropylene/polyethylene, polypropylene/polyester, polyropylene/polyamide, etc.

When the laminate is heated and pressed under state of the art conditions for molding such materials the layer 214 becomes highly densified and entraps the lateral fibers 21i6L to secure layers 214, 216 together while bonding layers 215 and 218B secure the outermost layers to the laminate.

The tough upper layer 212 resists cracking and shedding under the impact of direct user contact and flexing in use or when removed from a shoe but allows free flow of moisture vapor which is wicked through layer 214 to moisture storage layer 216 in an efficient way and retained there because of the bonded on moisture barrier 218A so that odor doesn't go beyond the innersole to any substantial degree. The overall result is an odor absorbing innersole of fibrous material that provides necessary cushioning in a slim profile that can fit comfortably in an athletic or dress shoe or boot or moccasin/loafer. No foam materials or charcoal adsorbents or the like need be used. Moisture can be absorbed in the present product and retained with high destruction of odor causing microbes and the moisture can desorb gradually with lowered concentrations of odor causing microbes with two to three ordor of magnitude reduction.

NAUTICAL FABRICS

Nautical fabrics can be made at least in part using the anti-microbial fibers of the present invention and are particularly useful for this type of application in which the fabrics are constantly wet and subject to mildew; and

MOLDABLE LAMINATES

Moldable laminates for footwear are described in more detail below. The present invention provides a binding agent in a nonwoven product in which the binding agent is a thermoplastic binder fiber or bi-component binder fiber. The binder fiber is thermally activated in order to bind (stiffen) the nonwoven portion of the product. Since this is produced with 100% thermoplastic components allows for easy recycling. The product is a thermal moldable impact resistant stiffener for footwear applications such a a counter or box toe.

A 100% thermoplastic, stiff reinforcing multiple laminate structure which can be moldable into complex, compound shapes and bondable via a thermoplastic hot melt adhesive to a carrier surface to be reinforced to provide a tough, water resistant reinforcement, usable for instance in stiffening applications as a footwear counter or box toe reinforcement element that is recyclable into itself. The fabric layer is in part geometrically locked into the tough thermoplastic resin layer.

Figure 26:
FIG. 26 is a cross section through a laminate for footwear components.

As shown in FIG. 26, the product comprises a tough extruded core of thermoplastic resin such as ionomer, EVA or styrene stiffened ionomer and at least one impact resistant strength layer of nonwoven.

The needle punched nonwoven is manufactured from a bi-component staple fiber or blend or PET staple fiber and binder staple fiber or blend of PET staple fiber and bi-component staple fiber. The nonwoven utilizes a combination of PET fibers and PETG or other copolymer or homopolymer fibers that act as a binding agent for PET. The staple fiber is 4–15 denier and 38 to 76 mm in length.

The thermoplastic components of the product are either miscible or mechanically compatible so as to allow for homogenization and incorporation into the extruded thermoplastic core thus allowing for complete recyclability of scrap material.

The binder fibers have a low melting temperature, and the fiber portion of the product is prepared as disclosed elsewhere herein.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A multi-component fiber of thermoplastic polymers, comprising:
   a. a core of thermoplastic polymer having at least 30 and less than 70% of the fiber by weight; and
   b. a sheath having more than 30% of the fiber by weight and including (i) a thermoplastic polymer and (ii) an anti-microbial/anti-fungal inorganic additive, and the additive in said sheath is from 0.1% to 20% by weight of fiber, the thickness of the sheath in microns being approximately two times the nominal particle size in microns of the additive.

2. A fiber as defined in claim 1 wherein the additive is selected from the group consisting of copper, zinc, tin and silver.

3. A fiber as defined in claim 2 wherein the additive is zeolite of silver.

4. A fiber as defined in claim 2 wherein said additive particles are approximately 1 micron cubes and the sheath is approximately 2 microns thick.

5. A fiber as defined in claim 2 wherein the additives are 0.2 to 6.0% by weight of the multi-part fiber.

6. A multi-part fiber as defined in claim 2 wherein the zeolite of silver is dispersed in a carrier of PE, PET, or PBT.

7. A multi-part fiber as defined in claim 2 wherein the first and second components are blended with a fiber which is selected from the group consisting of cotton, wool, polyester, acrylic and nylon and which is free of anti-microbial agents.

8. A fiber as defined in claim 5, wherein the polymers are of at least one chosen from the group consisting of PE, PP, PET (polyester), PCT, PETG, Co-PET, PTT, 3GT, and polyamide 6 or 6,6.

9. A fiber as defined in claim 1 wherein there is a second additive which is chosen from the group consisting of pigments, anti-odor compounds, fire-retardant, hydrophilic, and hydrophobic materials.

10. A fiber as defined in claim 6 wherein the fiber size ranges from 0.7 dTex to 25.0 dTex.

11. A fiber as defined in claim 8 wherein said fiber is cut staple in lengths from 1.0 mm to 180.0 mm.

12. A fiber as defined in claim 8 wherein the fiber is continuous filament.

13. A fiber as defined in claim 1 wherein the zeolite of silver is dispersed in a carrier of PE, PET, PETG or PBT and the additives are 0.2 to 6.0% by weight of the multi-part fiber.

14. A fiber as defined in claim 13 wherein the components are blended with a fiber which is selected from the group consisting of cotton, wool, polyester, acrylic and nylon and which is free of anti-microbial agents.

15. A multi-component fiber of thermoplastic polymer, comprising:

a. a core component of thermoplastic polymer having less than 70%, and at least 20% of the fiber by weight; and b. a sheath component surrounding the core component having more than 30% of the fiber by weight and including (i) a thermoplastic polymer and (ii) an anti-microbial/anti-fungal inorganic additive, the size of the inorganic additive with respect to the thickness of the sheath being such that the additive is firmly held in and strongly attached to the sheath, the size of the inorganic additive with respect to the thickness of the sheath being in an approximate ratio of 1:2.

16. A fiber as defined in claim 1 wherein the fiber is constructed and arranged so that some of the additive particles are exposed at the outer surface of the sheath and other of the additive particles are just below the outer surface of the sheath.

17. A fiber as defined in claim 1 wherein the additive is incorporated into the sheath polymer prior to the final extruding of the fiber.

* * * * *